United States Patent
Van Diepen et al.

(10) Patent No.: US 10,617,707 B2
(45) Date of Patent: Apr. 14, 2020

(54) OLIGONUCLEOTIDES TO TREAT EYE DISEASE

(71) Applicant: ProQR Therapeutics II B.V., Leiden (NL)

(72) Inventors: Hester Catharina Van Diepen, Leiden (NL); Hee Lam Chan, Leiden (NL); Janne Juha Turunen, Leiden (NL)

(73) Assignee: ProQR Therapeutics II B.V., Leiden (NL)

(*) Notice: Subject to any disclaimer, the term of this patent is extended or adjusted under 35 U.S.C. 154(b) by 0 days.

(21) Appl. No.: 16/096,038

(22) PCT Filed: Apr. 25, 2017

(86) PCT No.: PCT/EP2017/059830
§ 371 (c)(1),
(2) Date: Oct. 24, 2018

(87) PCT Pub. No.: WO2017/186739
PCT Pub. Date: Nov. 2, 2017

(65) Prior Publication Data
US 2019/0381089 A1 Dec. 19, 2019

(30) Foreign Application Priority Data
Apr. 25, 2016 (GB) .................. 1607141.7

(51) Int. Cl.
*A61K 31/7125* (2006.01)
*C12N 15/113* (2010.01)
*A61K 9/00* (2006.01)

(52) U.S. Cl.
CPC ........ *A61K 31/7125* (2013.01); *A61K 9/0048* (2013.01); *C12N 15/113* (2013.01); *C12N 2310/10* (2013.01); *C12N 2310/315* (2013.01); *C12N 2310/321* (2013.01)

(58) Field of Classification Search
None
See application file for complete search history.

(56) References Cited

U.S. PATENT DOCUMENTS

| 6,875,736 | B2 | 4/2005 | Rana |
| 2010/0048414 | A1 | 2/2010 | Weaver et al. |
| 2010/0196889 | A1 | 8/2010 | Bankaitis-Davis et al. |
| 2011/0070582 | A1 | 3/2011 | Bankaitis-Davis et al. |

FOREIGN PATENT DOCUMENTS

| EP | 1619249 | 9/2008 |
| EP | 2425814 | 6/2013 |
| WO | WO 02/024906 | 3/2002 |
| WO | WO2016/005514 | 1/2016 |
| WO | WO2017/060317 | 4/2017 |
| WO | WO2017/186739 | 11/2017 |

OTHER PUBLICATIONS

Bauer et al, "Recognition of nucleic acid and nucleic acid analogs by Toll-like receptors 7, 8 and 9," Immunobiology, 2008, 213:315-328.
Genbank Accession No. JA964943, "Sequence 47894 from Patent WO2012149438," dated Apr. 4, 2013, 1 page.
Genbank Accession No. JA980903, "Sequence 63854 from Patent WO2012149438," dated Apr. 4, 2013, 1 page.
Gorman et al., "Stable alteration of pre-mRNA splicing patterns by modified U7 small nuclear RNAs," Proc. Nall. Acad. Sci. USA, Apr. 1998, 95:4929-4934.
Lankveld et al, "In Vitro Testing for Direct Immunotoxicity: State of the Art," Methods Mol. Biol., 598:401-423.
Lenassi et al., "The effect of the common c.2299delG mutation in USH2A on RNA Splicing," Experimental Eye Research, 2014, 122:9-12.
McGee et al., "Novel mutations in the long isoform of the USH2A gene in patients with Usher syndrome type II or nonsyndromic retinitis pigmentosa," J. Med. Genet., Jul. 2010, 47:(7):499-506.
Milrpant et al., "Improved Antisense Oligonucleotide Design to Suppress Aberrant SMN2 Gene Transcript Processing: Towards a Treatment for Spinal Muscular Atrophy," PLOS ONE, Apr. 2013, 8:4:e62114.
O'Brien et al, "Investigation of the Alamar Blue (resazurin) fluorescent dye for the assessment of mammalian cell cytotoxicity," Eur. J. Biochem., 2000, 267:5421-5426.
Vache et al., "Usher syndrome type 2 caused by activation of an USH2A pseudoexon: implications for diagnosis and herapy," Wiley Periodicals, Inc., Human Genome Variation Society, 2011, 33:1:104-108.
Van Wijk et al., "Identification of 51 novel exons of the Usher syndrome type 2A {USH2A) gene that encode multiple conserved functional domains and that are mutated in patients with Usher syndrome type II," Am. J. Hum. Genet., 2004, 74:738-744.
PCT International Search Report in International Appln. No. PCT/EP2015/065736, dated Jun. 10, 2015, 6 pages.
PCT International Search Report and Written Opinion in International Appln. No. PCT/EP2017/059830, dated Aug. 3, 2017, 12 pages.
Kawasaki and Kawai, "Toll-like receptor signaling pathways," Front Immunol., 2014, 5:461.
Liquori, et al., "Whole USH2A gene sequencing identifies several new deep intronic mutations," Hum. Mutat., 2015, 37:184-193.
Zhong, et al., "Generation of three-dimensional retinal tissue with functional photoreceptors from human iPSCs," Nature Comm., 2014, 5:4047, 12 pages.

*Primary Examiner* — Sean McGarry
(74) *Attorney, Agent, or Firm* — Fish & Richardson P.C.

(57) ABSTRACT

The invention relates to the fields of medicine and immunology. In particular, it relates to novel antisense oligonucleotides that may be used in the treatment, prevention and/or delay of Usher Syndrome type II and/or USH2A-associated non syndromic retina degeneration, especially by skipping a pseudo exon (PE40) between exon 40 and 41 in the human USH2A gene.

15 Claims, 7 Drawing Sheets

Specification includes a Sequence Listing.

Fig.2

5'-*CUGCUUUCAG*CUUCCUCUCCAGAAUCACACAAGUUAAAGGACCCUUCUGCAACAAGAGCAGCAGGAAGCAGGAAGCUAAUA
3'-GUCGAAGGAGAGGUCUUAGUGUG-5' (1)
3'-GACGAAGUCGAAGGAGAGG-5' (17)
3'-GUGUUCAAUUUCCUGGAAG-5' (18)
(20) 3'-UCGUCCUUCGAUUAU

3'-AGACGUUGUCUCGUCGCUU-5' (3)
3'-AGACGUUGUCUCGUCGUCG-5' (5)
3'-AGAXGUUGUUXUXGUXGX-5' (7)
3'-GUUGUUCUCGUCGUCGCUUAGA-5' (19)
3'-ACGUUGUCUCGUCGCUUAG-5' (24)
3'-UUGUUCUCGUCGCUUAGAUG-5' (25)
3'-GUUCUCGUCGCUUAGAUGAG-5' (26)
3'-GUUXUXGUXGXUUAGAUGAG-5' (34)
3'-GUUXUXGUXGXUUAGAUGAG-5' (35)
3'-CGUCGCUUAGAUGAGUCG-5' (36)

AAAUGUAUGCUGGCUUUUAAGGGGAAACAAAUCAUGAAAUUGAACACCUCUCCUUUCCCAAG*GUAAGAGAUCAUCUUUAAGAAAAGG*
3'-ACAUACGACCGAAAUUCCC-5' (2)
UUUAC-5' (20)

3'-UGUUUAGUACUUUAACUUUAACUU-5' (21)
3'-CUUUAACUUUAACUUGUGGAG-5' (22)

3'-CCUUUGUUUAGUACUUUAACUUUA-5' (27)
3'-UUUGUUUAGUACUUUAACUUUAAC-5' (28)
3'-UUUAGUACUUUAACUUUAACUUGU-5' (29)

3'-CCAUUCUCUAGUAGAAAUUCUU-5' (4)
3'-CCAUUCUCUAGUAGAAAUUC-5' (6)
3'-XXAUUXUXUAGUAGAAAUX-5' (8)
3'-UUCCAUUCUCUAGUAGAAAUUC-5' (23)
3'-AGGGUUCCAUUCUCUAGUAGAA-5' (30)
3'-GGUUCCAUUCUCUAGUAGAAAU-5' (31)
3'-AUUCUCUAGUAGAAAUUCUUUCC-5' (32)
3'-XXAUUXUXUAGUAGAAAUUXUU-5' (37)

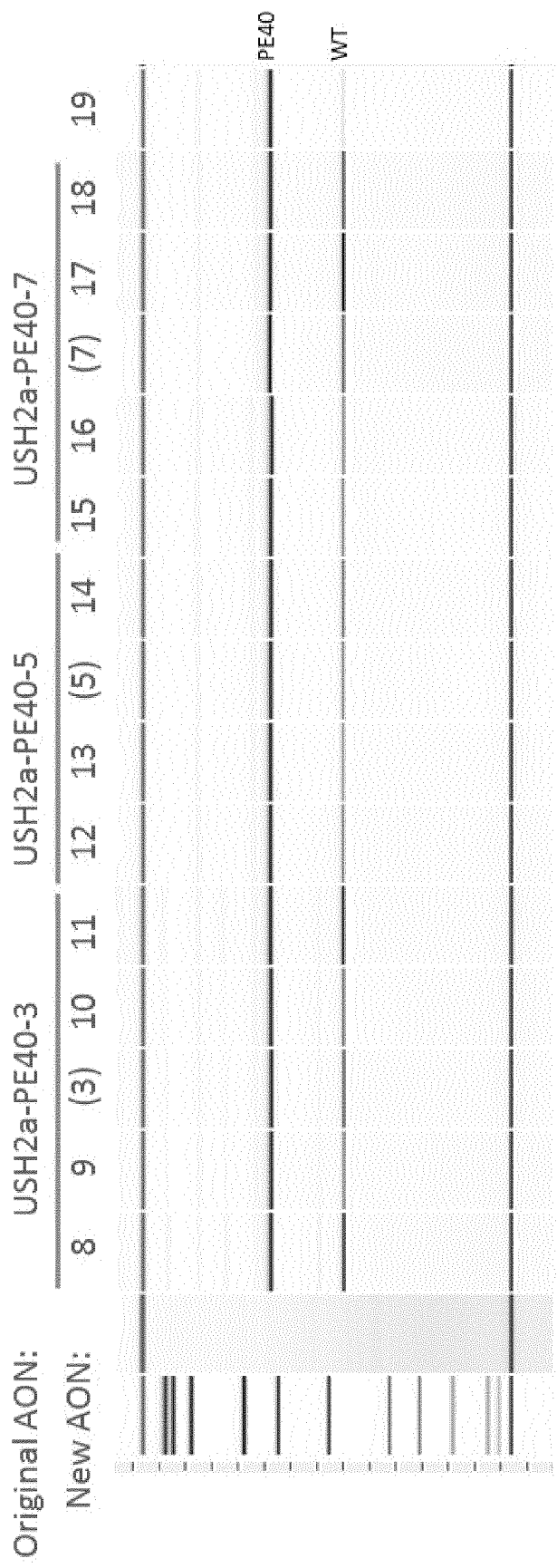

A

| | USH2a PE40-20 | | USH2a PE40-24 | | USH2a PE40-28 | | USH2a PE40-29 | | LPS | R848 |
| --- | --- | --- | --- | --- | --- | --- | --- | --- | --- | --- |
| | 1 μM | 4 μM | 1 μM | 4 μM | 1 μM | 4 μM | 1 μM | 4 μM | 100 ng/ml | 1 μM |
| IL-6 | 2.11 | 1.96 | 2.00 | 1.97 | 1.57 | 1.40 | 2.28 | 1.55 | 1172.88 | 602.93 |
| IL-1β | 2.46 | 2.28 | 1.88 | 2.33 | 1.64 | 1.79 | 2.06 | 1.81 | 1740.65 | 751.67 |
| IL-17 | 1.84 | 1.81 | 1.78 | 1.86 | 1.43 | 1.61 | 1.79 | 1.67 | 5.65 | 5.27 |
| IL-8 | 1.74 | 1.99 | 1.62 | 1.24 | 1.40 | 1.51 | 1.72 | 1.36 | 5.99 | 4.18 |
| MIP-1β | 1.89 | 2.05 | 1.64 | 1.82 | 1.35 | 1.58 | 1.60 | 1.52 | 7.17 | 8.37 |
| TNF-α | 1.74 | 1.84 | 1.45 | 1.69 | 1.20 | 1.32 | 1.45 | 1.37 | 341.31 | 136.70 |
| IFN-γ | 1.41 | 1.22 | 1.48 | 1.39 | 1.32 | 1.21 | 1.55 | 1.29 | 16.93 | 15.39 |
| IL-4 | 1.51 | 1.41 | 1.49 | 1.50 | 1.28 | 1.29 | 1.54 | 1.39 | 9.41 | 7.79 |
| IL-12 p70 | 1.24 | 1.37 | 1.38 | 1.67 | 1.15 | 1.46 | 1.37 | 1.46 | 5.56 | 6.14 |
| MCP-1 | 0.92 | 0.94 | 0.98 | 2.16 | 0.90 | 0.87 | 0.88 | 1.44 | 1.09 | 1.07 |

B

```
                        SEQUENCE LISTING

<160> NUMBER OF SEQ ID NOS: 48

<210> SEQ ID NO 1
<211> LENGTH: 23
<212> TYPE: RNA
<213> ORGANISM: Artificial Sequence
<220> FEATURE:
<223> OTHER INFORMATION: Antisense oligonucleotide

<400> SEQUENCE: 1
gugugauucu ggagaggaag cug                                           23

<210> SEQ ID NO 2
<211> LENGTH: 20
<212> TYPE: RNA
<213> ORGANISM: Artificial Sequence
<220> FEATURE:
<223> OTHER INFORMATION: Antisense oligonucleotide

<400> SEQUENCE: 2
cccuuaaaag ccagcauaca                                               20

<210> SEQ ID NO 3
<211> LENGTH: 20
<212> TYPE: RNA
<213> ORGANISM: Artificial Sequence
<220> FEATURE:
<223> OTHER INFORMATION: Antisense oligonucleotide

<400> SEQUENCE: 3
uucgcugcuc uuguugcaga                                               20

<210> SEQ ID NO 4
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 4
uucuuaaaga ugaucucuua cc                                            22

<210> SEQ ID NO 5
<211> LENGTH: 18
```

-continued

```
<212> TYPE: RNA
<213> ORGANISM: Artificial Sequence
<220> FEATURE:
<223> OTHER INFORMATION: Antisense oligonucleotide

<400> SEQUENCE: 5
cgcugcucuu guugcaga                                                18

<210> SEQ ID NO 6
<211> LENGTH: 20
<212> TYPE: RNA
<213> ORGANISM: Artificial Sequence
<220> FEATURE:
<223> OTHER INFORMATION: Antisense oligonucleotide

<400> SEQUENCE: 6
cuuaaagaug aucucuuacc                                              20

<210> SEQ ID NO 7
<211> LENGTH: 18
<212> TYPE: RNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: 1, 3, 6, 8, 15
<223> OTHER INFORMATION: n is 5-methyl-Cytosine (5mC)

<400> SEQUENCE: 7
ngnugnunuu guugnaga                                                18

<210> SEQ ID NO 8
<211> LENGTH: 20
<212> TYPE: RNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: 1, 13, 15, 19, 20
<223> OTHER INFORMATION: n is 5-methyl-Cytosine (5mC)

<400> SEQUENCE: 8
nuuaaagaug aununuuann                                              20

<210> SEQ ID NO 9
<211> LENGTH: 152
<212> TYPE: DNA
<213> ORGANISM: Artificial Sequence
<220> FEATURE:
<223> OTHER INFORMATION: Pseudo exon 40

<400> SEQUENCE: 9
cttcctctcc agaatcacac aagttaaagg acccttctgc aacaagagca gcgaatctac    60
tcagccagag caggaagcta ataaaatgta tgctggcttt taaggggggaa acaaatcatg   120 aaattgaaat tgaacaccte tcctttccca ag                                 152

<210> SEQ ID NO 10
<211> LENGTH: 20
<212> TYPE: DNA
<213> ORGANISM: Artificial Sequence
<220> FEATURE:
<223> OTHER INFORMATION: Part of Pseudo exon 40

<400> SEQUENCE: 10
```

```
tctgcaacaa gagcagcgaa                                          20

<210> SEQ ID NO 11
<211> LENGTH: 23
<212> TYPE: DNA
<213> ORGANISM: Artificial Sequence
<220> FEATURE:
<223> OTHER INFORMATION: Part of Pseudo exon 40

<400> SEQUENCE: 11
aggtaagaga tcatctttaa gaa                                      23

<210> SEQ ID NO 12
<211> LENGTH: 20
<212> TYPE: DNA
<213> ORGANISM: Artificial Sequence
<220> FEATURE:
<223> OTHER INFORMATION: Multiplex ddPCR primer and probe

<400> SEQUENCE: 12
tccaatggat ttggcagtgc                                          20

<210> SEQ ID NO 13
<211> LENGTH: 20
<212> TYPE: DNA
<213> ORGANISM: Artificial Sequence
<220> FEATURE:
<223> OTHER INFORMATION: Multiplex ddPCR primer and probe

<400> SEQUENCE: 13
gttctcaagt atagacggcc                                          20

<210> SEQ ID NO 14
<211> LENGTH: 20
<212> TYPE: DNA
<213> ORGANISM: Artificial Sequence
<220> FEATURE:
<223> OTHER INFORMATION: Multiplex ddPCR primer and probe

<400> SEQUENCE: 14
gccaggtgac caacatcatt                                          20

<210> SEQ ID NO 15
<211> LENGTH: 18
<212> TYPE: DNA
<213> ORGANISM: Artificial Sequence
<220> FEATURE:
<223> OTHER INFORMATION: Multiplex ddPCR primer and probe

<400> SEQUENCE: 15
cagccagagc aggaagct                                            18

<210> SEQ ID NO 16
<211> LENGTH: 18
<212> TYPE: DNA
<213> ORGANISM: Artificial Sequence
<220> FEATURE:
<223> OTHER INFORMATION: Multiplex ddPCR primer and probe

<400> SEQUENCE: 16
gcagaggaca aacctgga                                            18

<210> SEQ ID NO 17
<211> LENGTH: 20
<212> TYPE: RNA
<213> ORGANISM: Artificial Sequence
```

```
<220> FEATURE:
<223> OTHER INFORMATION: Antisense oligonucleotide

<400> SEQUENCE: 17
ggagaggaag cugaaagcag                                               20

<210> SEQ ID NO 18
<211> LENGTH: 20
<212> TYPE: RNA
<213> ORGANISM: Artificial Sequence
<220> FEATURE:
<223> OTHER INFORMATION: Antisense oligonucleotide

<400> SEQUENCE: 18
gaaggguccu uuacuugug                                                20

<210> SEQ ID NO 19
<211> LENGTH: 19
<212> TYPE: RNA
<213> ORGANISM: Artificial Sequence
<220> FEATURE:
<223> OTHER INFORMATION: Antisense oligonucleotide

<400> SEQUENCE: 19
agauucgcug cucuuguug                                                19

<210> SEQ ID NO 20
<211> LENGTH: 20
<212> TYPE: RNA
<213> ORGANISM: Artificial Sequence
<220> FEATURE:
<223> OTHER INFORMATION: Antisense oligonucleotide

<400> SEQUENCE: 20 cauuuauua gcuuccugcu                                                20

<210> SEQ ID NO 21
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 21
uucaauuuca auucaugau uugu                                           24

<210> SEQ ID NO 22
<211> LENGTH: 21
<212> TYPE: RNA
<213> ORGANISM: Artificial Sequence
<220> FEATURE:
<223> OTHER INFORMATION: Antisense oligonucleotide

<400> SEQUENCE: 22
gagguguuca auucaauuu c                                              21

<210> SEQ ID NO 23
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 23
cuuaaagaug aucucuuacc uu                                            22
```

<210> SEQ ID NO 24
<211> LENGTH: 20
<212> TYPE: RNA
<213> ORGANISM: Artificial Sequence
<220> FEATURE:
<223> OTHER INFORMATION: Antisense oligonucleotide

<400> SEQUENCE: 24
gauucgcugc ucuuguugca                                               20

<210> SEQ ID NO 25
<211> LENGTH: 20
<212> TYPE: RNA
<213> ORGANISM: Artificial Sequence
<220> FEATURE:
<223> OTHER INFORMATION: Antisense oligonucleotide

<400> SEQUENCE: 25
guagauucgc ugcucuuguu                                               20

<210> SEQ ID NO 26
<211> LENGTH: 20
<212> TYPE: RNA
<213> ORGANISM: Artificial Sequence
<220> FEATURE:
<223> OTHER INFORMATION: Antisense oligonucleotide

<400> SEQUENCE: 26
gaguagauuc gcugcucuug                                               20

<210> SEQ ID NO 27
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 27
auuucaauuu caugauuugu uucc                                          24

<210> SEQ ID NO 28
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 28
caauuucaau uucaugauuu guuu                                          24

<210> SEQ ID NO 29
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 29
uguucaauuu caauuucaug auuu                                          24

<210> SEQ ID NO 30
<211> LENGTH: 22
<212> TYPE: RNA
<213> ORGANISM: Artificial Sequence
<220> FEATURE:
<223> OTHER INFORMATION: Antisense oligonucleotide

```
<400> SEQUENCE: 30
aagaugaucu cuuaccuugg ga                                      22

<210> SEQ ID NO 31
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 31
uaaagaugau cucuuaccuu gg                                      22

<210> SEQ ID NO 32
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 32
ccuuuucuua aagaugaucu cuua                                    24

<210> SEQ ID NO 33
<211> LENGTH: 21
<212> TYPE: RNA
<213> ORGANISM: Artificial Sequence
<220> FEATURE:
<223> OTHER INFORMATION: Antisense oligonucleotide

<400> SEQUENCE: 33
caaaccccca caauacacag c                                       21

<210> SEQ ID NO 34
<211> LENGTH: 20
<212> TYPE: RNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: 3, 5, 8, 10, 17
<223> OTHER INFORMATION: n is 5-methyl-Cytosine (5mC)

<400> SEQUENCE: 34
uungnugnun uuguugnaga                                         20

<210> SEQ ID NO 35
<211> LENGTH: 20
<212> TYPE: RNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: 10, 12, 15, 17
<223> OTHER INFORMATION: n is 5-methyl-Cytosine (5mC)

<400> SEQUENCE: 35
gaguagauun gnugnunuug                                         20

<210> SEQ ID NO 36
<211> LENGTH: 18
<212> TYPE: RNA
<213> ORGANISM: Artificial Sequence
<220> FEATURE:
```

```
<223> OTHER INFORMATION: Antisense oligonucleotide

<400> SEQUENCE: 36
gcugaguaga uucgcugc                                                  18

<210> SEQ ID NO 37
<211> LENGTH: 22
<212> TYPE: RNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: 3, 15, 17, 21, 22
<223> OTHER INFORMATION: n is 5-methyl-Cytosine (5mC)

<400> SEQUENCE: 37
uunuuaaaga ugaununuua nn                                             22

<210> SEQ ID NO 38
<211> LENGTH: 22
<212> TYPE: RNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: 6, 7, 8, 10, 13, 20
<223> OTHER INFORMATION: n is 2, 6-diaminopurine (DAP)

<400> SEQUENCE: 38
uucuunnngn ugnucucuun cc                                             22

<210> SEQ ID NO 39
<211> LENGTH: 22
<212> TYPE: RNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: 3, 15, 17, 21, 22
<223> OTHER INFORMATION: n is 5-methyl-Cytosine (5mC)
<220> FEATURE:
<221> NAME/KEY: misc_feature
<222> LOCATION: 6, 7, 8, 10, 13, 20
<223> OTHER INFORMATION: n is 2, 6-diaminopurine (DAP)

<400> SEQUENCE: 39
uunuunnngn ugnununuun nn                                             22

<210> SEQ ID NO 40
<211> LENGTH: 21
<212> TYPE: DNA
<213> ORGANISM: Artificial Sequence
<220> FEATURE:
<223> OTHER INFORMATION: PCR Primer

<400> SEQUENCE: 40
gctctcccag ataccaactc c                                              21

<210> SEQ ID NO 41
<211> LENGTH: 20
<212> TYPE: DNA
<213> ORGANISM: Artificial Sequence
<220> FEATURE:
<223> OTHER INFORMATION: PCR Primer

<400> SEQUENCE: 41
```

```
gattcacatg cctgaccctc                                                    20

<210> SEQ ID NO 42
<211> LENGTH: 13
<212> TYPE: RNA
<213> ORGANISM: Artificial Sequence
<220> FEATURE:
<223> OTHER INFORMATION: Antisense oligonucleotide overlapping sequence

<400> SEQUENCE: 42
agaugaucuc uua                                                           13

<210> SEQ ID NO 43
<211> LENGTH: 6
<212> TYPE: RNA
<213> ORGANISM: Artificial Sequence
<220> FEATURE:
<223> OTHER INFORMATION: Antisense oligonucleotide overlapping sequence

<400> SEQUENCE: 43 cgcugc                                                                    6

<210> SEQ ID NO 44
<211> LENGTH: 18
<212> TYPE: RNA
<213> ORGANISM: Artificial Sequence
<220> FEATURE:
<223> OTHER INFORMATION: Antisense oligonucleotide overlapping sequence

<400> SEQUENCE: 44
auuucaauuu caugauuu                                                      18

<210> SEQ ID NO 45
<211> LENGTH: 32
<212> TYPE: RNA
<213> ORGANISM: Artificial Sequence
<220> FEATURE:
<223> OTHER INFORMATION: Antisense oligonucleotide target sequence

<400> SEQUENCE: 45
ucccaaggua agagaucauc uuuaagaaaa gg                                      32

<210> SEQ ID NO 46
<211> LENGTH: 30
<212> TYPE: RNA
<213> ORGANISM: Artificial Sequence
<220> FEATURE:
<223> OTHER INFORMATION: Antisense oligonucleotide target sequence

<400> SEQUENCE: 46
ucugcaacaa gagcagcgaa ucuacucagc                                         30

<210> SEQ ID NO 47
<211> LENGTH: 30
<212> TYPE: RNA
<213> ORGANISM: Artificial Sequence
<220> FEATURE:
<223> OTHER INFORMATION: Antisense oligonucleotide target sequence

<400> SEQUENCE: 47
ggaaacaaau caugaaauug aaauugaaca                                         30

<210> SEQ ID NO 48
<211> LENGTH: 187
<212> TYPE: DNA
```

```
<213> ORGANISM: Artificial Sequence
<220> FEATURE:
<223> OTHER INFORMATION: Pseudo exon 40 and flanking sequences

<400> SEQUENCE: 48
ctgctttcag cttcctctcc agaatcacac aagttaaagg acccttctgc aacaagagca      60
gcgaatctac tcagccagag caggaagcta ataaaatgta tgctggcttt taagggggaa     120
acaaatcatg aaattgaaat tgaacacctc tcctttccca aggtaagaga tcatctttaa     180
gaaaagg                                                               187
```

OLIGONUCLEOTIDES TO TREAT EYE DISEASE

RELATED APPLICATIONS

This application is a § 371 National Stage Application of PCT/EP2017/059830, filed Apr. 25, 2017, which claims priority to and the benefit of United Kingdom patent application No. 1607141.7, filed Apr. 25, 2016, the entire disclosures of each of which are incorporated herein by reference for all purposes.

FIELD OF THE INVENTION

The invention relates to the fields of medicine and immunology. In particular, it relates to novel antisense oligonucleotides for the treatment, prevention and/or delay of Usher Syndrome type II and/or USH2A-associated non syndromic retina degeneration.

BACKGROUND OF THE INVENTION

Usher Syndrome (USH) and non-syndromic retinitis pigmentosa (NSRP) are degenerative diseases of the retina. USH is clinically and genetically heterogeneous and by far the most common type of inherited deaf-blindness in humans. The hearing impairment in USH patients is mostly stable and congenital and can be partly compensated by hearing aids or cochlear implants. NSRP is more prevalent than USH, occurring in 1 per 4,000 individuals. The degeneration of photoreceptor cells in USH and NSRP is progressive and often leads to complete blindness between the third and fourth decade of life, thereby leaving time for therapeutic intervention. Mutations in the USH2A gene are the most frequent cause of both disorders. The range of mutations is spread throughout all 72 USH2A exons and their flanking intron sequences, and contains nonsense and missense mutations, deletions, duplications, large rearrangements, and splicing variants. The by far most frequently mutated exon is exon 13, which contains two founder mutations (c.2299delG (p.E767SfsX21) in Usher Syndrome type II (USH2) patients and c.2276G>T (p.C759F) in NSRP patients). For exon 50, fifteen pathogenic mutations have been reported, of which at least eight are clearly protein truncating. The first deep-intronic mutation in intron 40 of USH2A (c.7595-2144A>G) was reported by Vaché et al (2012. Hum Mutat 33:104-8). This mutation creates a cryptic high-quality splice donor site in intron 40 resulting in the inclusion of an aberrant exon of 152 bp in the mutant USH2A mRNA, and leading to premature termination of translation (see FIGS. 1A and B of WO 2016/005514).

USH and other retinal dystrophies have for long been considered as incurable disorders. However, several phase I/II clinical trials using gene augmentation therapy have led to promising results in selected groups of LCA/RP/USH patients with mutations in the RPE65 and MYO7A genes. The size of the coding sequence (15,606 bp) and alternative splicing of the USH2A gene and mRNA, respectively, hamper gene augmentation therapy, due to the currently limiting cargo size of many available vectors (e.g. adeno-associated (AAV) and lentiviral vectors).

Despite the broad clinical potential of antisense oligonucleotide (AON)-based therapy, it is not frequently used in the vertebrate eye. AONs are small (16-25 nucleotide) polynucleotide molecules that are able to interfere with splicing as their sequence is complementary to that of target pre-mRNA molecules. Upon binding of an AON, the targeted region of the pre-mRNA is no longer available for splicing factors which results in skipping of the exon that is targeted by the AON. Therapeutically, this methodology can be used in two ways: a) to redirect normal splicing of genes in which mutations activate cryptic splice sites and b) to skip exons that carry (protein-truncating) mutations in such a way, that the reading frame of the mRNA remains intact and a (partially) functional protein is made. For the USH2A gene, 28 of the 72 exons can potentially be skipped without disturbing the overall reading frame of the transcript. Both AON-based methods are being successfully applied in patients with severe genetic disorders. Liguori et al. (2016. Hum Mutat 37:184-193) showed that an AON could prevent the inclusion of a 155 bp pseudo exon 50 (PE 50), caused by the c.9959.4159A>G mutation in intron 50, in the mRNA of the USH2A gene.

It is an objective of the invention to provide a convenient therapeutic strategy for the prevention, treatment or delay of USH and/or NSRP caused by the c.7595-2144A>G mutation present in the intron between exon 40 and 41 of the human USH2A gene. It has previously been suggested (Vaché et al. 2012) and thereafter demonstrated (WO 2016/005514) that AONs are able to block the aberrant splicing of USH2A pre-mRNA that is caused by this mutation leading to the inclusion of pseudo exon 40: PE40. Notably, there is a need for further improved alternatives that perform better and that have additional beneficial properties. An objective of the present invention is to provide such alternatives.

SUMMARY OF THE INVENTION

The present invention relates to an antisense oligonucleotide (AON) that is able to induce skipping of pseudo exon 40 (PE40) from human USH2A pre-mRNA, wherein the inclusion of the pseudo exon is due to the c.7595-2144A>G in the USH2A gene, and wherein said AON comprises a sequence selected from any of the following groups of sequences: (i) SEQ ID NO:6, 4, 8, 23, 30, 31, 32, 37; (ii) SEQ ID NO:3, 5, 7, 19, 24, 25, 26, 34, 35, 36; and (iii) SEQ ID NO:21, 27, 28, 29. The invention, in another embodiment, also relates to an AON that is capable to inducing skipping of PE40 from human USH2A pre-mRNA, wherein said AON comprises a sequence that is complementary to at least 18, 19, 20, 21, 22, 23, or 24 consecutive nucleotides of SEQ ID NO:45, 46 or 47. In a preferred embodiment, the AON of the present invention has a length of 18 to 143 nucleotides, preferably 18 to 40 nucleotides, more preferably 18 to 30 nucleotides, even more preferably 18 to 24 nucleotides, and most preferably consists of a sequence selected from the group consisting of SEQ ID NO:6, 3, 4, 5, 7, 8, 19, 21, 23, 24, 25, 26, 27, 28, 29, 30, 31, 32, 34, 35, 36, and 37, preferably selected from SEQ ID NO:6, 3, 4, 5, 7, 8, 26, 34, 35, and 37, more preferably selected from SEQ ID NO:6, 3, 4, 5, 7, 8, 26, and 35. In another preferred embodiment, the AON according to the invention comprises a 2'-O-alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives. One or more nucleotides within the AON of the present invention may be modified by a 2'-O-methoxyethyl modification. The invention further relates to a set of AONs comprising at least two AONs as claimed herein. In another embodiment, the invention also relates to a viral vector expressing an AON according to the invention, when placed under conditions conducive to expression of the AON. In yet another embodiment, the invention relates to a pharmaceutical composition comprising an AON according to the invention, or a set of AONs according to the invention, or a viral vector according to the invention, and a pharmaceutically acceptable excipient. The invention further relates to an AON, a set, a vector or a composition according to the invention, for use in the treatment of a USH2A related disease or condition, such as Usher Syndrome type II, requiring modulating splicing of USH2A pre-mRNA.

BRIEF DESCRIPTION OF THE DRAWINGS

FIG. 2 shows the PE40 sequence (bold and underlined, and split in two parts) from 5' to 3', and the binding sites for the different AONs tested herein. The SEQ ID NO of each tested AON is given between brackets, names are given in Table 1. The first nucleotide downstream of the PE40 sequence is a guanosine (G) which represents the c.7595-2144A>G mutation. Positions for AON1 (1) and AON2 (2) are given directly below the PE40 sequence. Italic sequences are up- and downstream sequences of PE40. The three areas of interest, as outlined in the examples, and as claimed herein, surround USH2a-PE40-3 (SEQ ID NO:19, bold), USH2a-PE40-5 (SEQ ID NO:21, bold) and USH2a-PE40-7 (SEQ ID NO:23, bold) respectively.

FIG. 3 shows the reverse transcriptase results of the PE40 skip screening of a set of oligonucleotides that were based on USH2a-PE40-3, -5 and -7, shown in FIGS. 1 and 2. Clearly, AONs USH2a-PE40-8 and -11 (based on USH2a-PE40-3) and USH2a-PE40-17 (based on USH2a-PE40-7) showed a further increased intensity, suggesting a further improvement over the known oligonucleotides from the art.

DETAILED DESCRIPTION

Figure 1:
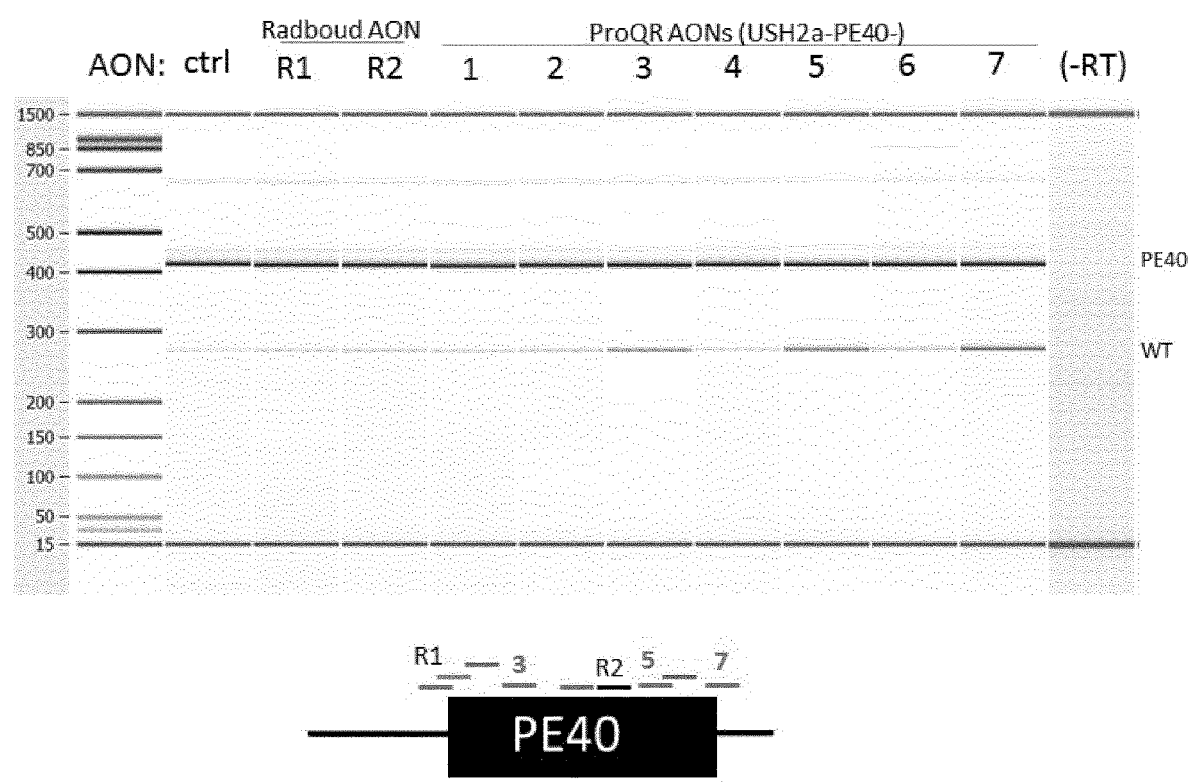
FIG. 1 shows the reverse transcriptase results of the initial screening of seven alternative antisense oligonucleotides that were compared for PE40 exon skipping efficiency in comparison with two known antisense oligonucleotides from the art (AON1 and AON2: R1 and R2 respectively) and an unrelated control oligonucleotide (ctrl), using a reporter construct in HEK293 cells, showing a clear increase in signal after administering USH2a-PE40-3, -5 and -7. The lower panel shows the approximate positions of the different AONs in respect of the PE40 sequence.

For the purpose of the invention the terms "the inclusion of aberrant pseudo exon", "the inclusion of aberrant pseudo exon 40" or "the inclusion of aberrant 152 bp nucleotide pseudo exon" are considered to be synonymous, and considered to mean the inclusion of pseudo exon 40 (PE40) of the USH2A gene into the mRNA, or the inclusion of a part thereof or a sequence comprising 90, 91, 92, 93, 94, 95, 96, 97, 98, 99 or 100% of that sequence into the USH2A mRNA. The term "exon skipping" is herein defined as inducing, producing or increasing production within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with an exon inclusion signal required for recognition of a stretch of nucleotides as an exon to be included in the mature mRNA; such molecules are herein referred to as exon skipping molecules. In the present invention exon skipping relates to skipping PE40.

The term "pre-mRNA" refers to a non-processed or partly processed precursor mRNA that is synthesized from a DNA template of a cell by transcription, such as in the nucleus.

The term "exon retention" relates to the production within a cell of a mature mRNA that includes a particular exon when no exon skipping of that exon has taken place while processing the pre-mRNA through the splicing reaction. With respect to the present invention, PE40 that is normally not present in the mature mRNA from the human USH2A gene when it is wild type, retains in the mature mRNA from the human USH2A gene when a particular mutation makes that the PE40 is not spliced out from the pre-mRNA, as occurs in the presence of the c.7595-2144A>G mutation as discussed in detail herein. The aim of the present invention is to prevent, inhibit, or reduce exon retention of PE40 in the human USH2A mRNA, thereby preventing, delaying and/or treating Usher Syndrome type II.

The term "antisense oligonucleotide" (AON) is understood to refer to a nucleotide sequence that is substantially complementary to a target nucleotide sequence in a pre-mRNA molecule, heterogeneous nuclear RNA (hnRNA) or mRNA molecule. The target sequences of the oligonucleotides of the present invention are provided herein. The degree of complementarity (or substantial complementarity) of the antisense sequence is preferably such that a molecule comprising the antisense sequence can form a stable hybrid with the target nucleotide sequence in the RNA molecule under physiological conditions. The terms "antisense oligonucleotide", its abbreviation "AON" and the term "oligonucleotide" are used interchangeably herein and are understood to refer to an oligonucleotide comprising an antisense sequence. The antisense oligonucleotide is preferably single-stranded and preferably does not self-anneal, either to itself or another AON of the same kind.

The term "substantially complementary" used in the context of the invention indicates that some mismatches in the antisense sequence are allowed as long as the functionality, i.e. inducing skipping of PE40 is still acceptable.

The term "pseudo exon skipping" is herein defined as inducing, stimulating, causing, enhancing, producing or increasing production within a cell of a mature mRNA that does not contain a particular intronic region or pseudo exon that would be present in the mature mRNA without pseudo exon skipping. Pseudo exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with a pseudo exon inclusion signal required for recognition of a stretch of nucleotides as a pseudo exon to be included in the mature mRNA; such molecules are herein referred to as pseudo exon skipping molecules.

Preferably, the complementarity is from 90% to 100%. In general this allows for 1 or 2 mismatches in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

In an embodiment, an exon skipping AON as defined herein can be a compound that binds and/or is complementary to a specified sequence. Methods for screening AONs that bind specific nucleotide sequences are, for example, disclosed in WO 2002/024906, U.S. Pat. No. 6,875,736 and WO 2016/005514, which are herein incorporated by reference. Binding to specified sequences, preferably in the context of the aberrant 152 nucleotide USH2A pseudo exon 40 (PE40), may be assessed via techniques known to the skilled person. A preferred technique is gel mobility shift assay as described in EP1619249. In a preferred embodiment, a (pseudo) exon skipping AON is said to bind as soon as a binding of said molecule to a labeled sequence is detectable in a gel mobility shift assay.

In all embodiments of the invention, a "(pseudo) exon skipping molecule" is an AON. Designing an AON for the purpose of the present invention is of particular relevance. In a preferred method at least one of the following aspects has to be taken into account for designing, improving said exon skipping molecule: (1) the AON preferably does not contain a CpG or a stretch of CpG motifs; and (2) the AON has acceptable RNA binding kinetics and/or thermodynamic properties. The presence of CpG or a stretch of CpG motifs in an oligonucleotide is usually associated with an increased immunogenicity of said oligonucleotide. Immunogenicity may be assessed in an animal model by assessing the presence of CD4+ and/or CD8+ cells and/or inflammatory mononucleocyte infiltration. It may also be assessed in blood of an animal or of a human being treated with an oligonucleotide of the invention by detecting the presence of a neutralizing antibody and/or an antibody recognizing said oligonucleotide using a standard immunoassay known to the skilled person. An inflammatory reaction, type I-like interferon production, IL-12 production and/or an increase in immunogenicity may be assessed by detecting the presence or an increasing amount of a neutralizing antibody or an antibody recognizing said oligonucleotide using a standard immunoassay.

The invention relates to an AON with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/-cail/biotool/oligo/index.html) for single stranded RNA using the basic Tm and the nearest neighbor model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 70° C. and an acceptable free energy may be ranged between 15 and 45 kcal/mol.

In a preferred embodiment, an AON is said to induce skipping of the aberrant 152 nucleotide USH2A pseudo exon 40 (SEQ ID NO:5 in WO 2016/005514), when the aberrant 152 nucleotide USH2A pseudo exon 40 skipping percentage as measured by real-time quantitative RT-PCR analysis is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%. Preferred assays to determine exon skipping and/or exon retention are described in the examples herein.

Preferably, an AON according to the invention comprises a sequence that is complementary or substantially complementary to a nucleotide sequence of PE40 (SEQ ID NO:9 herein), or part thereof such that the (substantially) complementary part is at least 50% of the length of the oligonucleotide according to the invention, more preferably at least 60%, even more preferably at least 70%, even more preferably at least 80%, even more preferably at least 90% or even more preferably at least 95%, or even more preferably 98% or even more preferably at least 99%, or even more preferably 100%. Preferably, an AON according to the invention comprises or consists of a sequence that is complementary to a part of SEQ ID NO:9, shown below:

```
Pseudo exon 40; PE40
                                    (SEQ ID NO: 9)
5'-CTTCCTCTCCAGAATCACACAAGTTAAAGGACCCTTCTGCAACAAG

AGCAGCGAATCTACTCAGCCAGAGCAGGAAGCTAATAAAATGTATGCTG

GCTTTTAAGGGGGAAACAAATCATGAAATTGAAATTGAACACCTCTCCT

TTCCCAAG-3'
```

As an example, an AON may comprise a sequence that is complementary to part of SEQ ID NO:9 and additional flanking sequences, especially the splice site at the 3' end of PE40. In a more preferred embodiment, the length of said complementary part of said AON is of at least 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides. Additional flanking sequences may be used to modify the binding, or to modify a thermodynamic property of the AON, more preferably to modify target RNA binding affinity. The skilled person knows that it is thus not absolutely required that all the bases in the region of complementarity are capable of pairing with bases in the opposing strand. For instance, when designing the AON one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" preferably means that using a gel mobility shift assay as described in example 1 of EP1619249, binding of an AON is detectable.

Optionally, said AON may further be tested by transfection into fibroblasts or retina cells of patients. Skipping of a targeted exon may be assessed by RT-PCR (such as e.g. described in EP1619249). The complementary regions are preferably designed such that, when combined, they are specific for the exon in the pre-mRNA. Such specificity may be created with various lengths of complementary regions as this depends on the actual sequences in other (pre) mRNA molecules in the system. The risk that the AON also will be able to hybridize to one or more other pre-mRNA molecules decreases with increasing size of the AON. It is clear that AONs comprising mismatches in the region of complementarity but that retain the capacity to hybridize and/or bind to the targeted region(s) in the pre-mRNA, can be used in the invention. However, preferably at least the complementary parts do not comprise such mismatches as AONs lacking mismatches in the complementary part typically have a higher efficiency and a higher specificity, than AONs having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%.

A pseudo exon skipping AON of the invention is preferably in an isolated form. A preferred pseudo exon skipping AON according to the invention has a length from 18 to 143 nucleotides, more preferred from 18 to 60, more preferred 18 to 40 nucleotides, more preferred from 18 to 30 nucleotides, more preferred from 18 to 24 nucleotides, most preferred 18 nucleotides, 19 nucleotides, 20 nucleotides, 21 nucleotides, 22 nucleotides, 23 nucleotides, or 24 nucleotides. In another preferred embodiment the AON of the invention consists of from 18 to 143 nucleotides, more preferred from 18 to 40 nucleotides, more preferred from 18 to 30 nucleotides, more preferred from 18 to 20 nucleotides, or preferably consists of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

It is preferred that an exon skipping AON of the invention comprises one or more residues that are modified to increase nuclease resistance, and/or to increase the affinity of the AON for the target sequence. Therefore, in a preferred embodiment, the AON sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNaseH. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium. It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages. A preferred nucleotide analogue or equivalent comprises a Peptide Nucleic Acid (PNA), having a modified polyamide backbone. PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer. Since the backbone of a PNA molecule contains no charged phosphate groups, PNA-RNA hybrids are usually more stable than RNA-RNA or RNA-DNA hybrids, respectively. A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage. In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate. A further preferred nucleotide analogue or equivalent of the invention comprises one or more sugar moieties that are mono- or disubstituted at the 2', 3' and/or 5' position such as a —OH; —F; substituted or unsubstituted, linear or branched lower (CI-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-P, 4'-C-ethylene-bridged nucleic acid. These substitutions render the nucleotide analogue or equivalent RNase H and nuclease resistant and increase the affinity for the target RNA. In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art. It is understood by a skilled person that it is not necessary for all positions in an AON to be modified uniformly. In addition, more than one of the aforementioned analogues or equivalents may be incorporated in a single AON or even at a single position within an AON. In certain embodiments, an AON of the invention has at least two different types of analogues or equivalents.

A preferred pseudo exon skipping AON according to the invention is a 2'-O alkyl phosphorothioate AON, such as 2'-O-methyl modified ribose (RNA), 2'-O-ethyl modified ribose, 2'-O-propyl modified ribose, and/or substituted derivatives of these modifications such as halogenated derivatives. An effective AON according to the invention comprises a 2'-O-methyl ribose with a phosphorothioate backbone.

It will also be understood by a skilled person that different AONs can be combined for efficiently skipping of the aberrant 152 nucleotide pseudo exon of USH2A. In a preferred embodiment, a combination (or set) of at least 2, 3, 4, 5 or 6 AONs are used in a method of the invention.

An AON can be linked to a moiety that enhances uptake of the AON in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An AON according to the invention may be indirectly administrated using suitable means known in the art. It may for example be provided to an individual or a cell, tissue or organ of said individual in the form of an expression vector wherein the expression vector encodes a transcript comprising said AON. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an exon skipping molecule as identified herein. Accordingly, the invention provides a viral vector expressing an AON according to the invention when placed under conditions conducive to expression of the AON. A cell can be provided with an AON capable of interfering with essential sequences that result in highly efficient skipping of the aberrant 152 nucleotide USH2A pseudo exon by plasmid-derived AON expression or viral expression provided by adenovirus- or adeno-associated virus-based vectors. Expression may be driven by a polymerase II-promoter (Pol II) such as a U7 promoter or a polymerase III (Pol III) promoter, such as a U6 RNA promoter. A preferred delivery vehicle is a viral vector such as an adeno-associated virus vector (AAV), or a retroviral vector such as a lentivirus vector and the like, all as described in detail in WO 2016/005514. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from Pol-III promoters, and/or wherein transcripts are in the form fusions with U1 or U7 transcripts, which yield good results for delivering small transcripts. It is within the skill of the artisan to design suitable transcripts. Preferred are Pol-III driven transcripts, preferably, in the form of a fusion transcript with an U1 or U7 transcript.

The AON according to the invention may be delivered as such. However, the AON may also be encoded by the viral vector. Typically, this is in the form of an RNA transcript that comprises the sequence of an AON according to the invention in a part of the transcript.

Improvements in means for providing an individual or a cell, tissue, organ of said individual with an AON according to the invention, are anticipated considering the progress that has already thus far been achieved. Such future improvements may of course be incorporated to achieve the mentioned effect on restructuring of mRNA using a method of the invention. An AON according to the invention can be delivered as is to an individual, a cell, tissue or organ of said individual. When administering an AON according to the invention, it is preferred that the molecule is dissolved in a solution that is compatible with the delivery method. Retina or inner ear cells can be provided with a plasmid for AON expression by providing the plasmid in an aqueous solution or thorough a viral vector or nanoparticles, all as described in detail in WO 2016/005514. Preferably viral vectors or nanoparticles are delivered to retina or inner ear cells. The skilled person may select and adapt any of the known and/or other commercially available alternative excipients and delivery systems to package and deliver an AON for use in the current invention to deliver it for the prevention, treatment or delay of a USH2A related disease or condition. "Prevention, treatment or delay of a USH2A related disease or condition" is herein preferably defined as preventing, halting, ceasing the progression of, or reversing partial or complete visual impairment or blindness, as well as preventing, halting, ceasing the progression of or reversing partial or complete auditory impairment or deafness that is caused by a genetic defect in the USH2A gene.

In a preferred embodiment, an AON according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound, each constituent of the composition may not be formulated in one single combination or composition or preparation. Depending on their identity, the skilled person will know which type of formulation is the most appropriate for each constituent as defined herein. If required, an AON according to the invention or a vector, preferably a viral vector, expressing an AON according to the invention can be incorporated into a pharmaceutically active mixture by adding a pharmaceutically acceptable carrier.

Accordingly, the invention also provides a composition, preferably a pharmaceutical composition, comprising an AON according to the invention, or a viral vector according to the invention and a pharmaceutically acceptable excipient. Such composition may comprise a single AON or viral vector according to the invention, but may also comprise multiple, distinct AONs or viral vectors according to the invention. Such a pharmaceutical composition may comprise any pharmaceutically acceptable excipient, including a carrier, filler, preservative, adjuvant, solubilizer and/or diluent.

A preferred route of administration is through intravitreal injection of an aqueous solution or specially adapted formulation for intraocular administration. EP2425814 discloses an oil in water emulsion especially adapted for intraocular (intravitreal) administration of peptide or nucleic acid drugs. This emulsion is less dense than the vitreous fluid, so that the emulsion floats on top of the vitreous, avoiding that the injected drug impairs vision.

If multiple distinct AONs according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of AONs according to the invention used is dosed in an amount ranged from 0.01 and 20 mg/kg, preferably from 0.05 to 20 mg/kg. A suitable intravitreal dose would be between about 0.05 and about 5 mg, preferably between about 0.1 and about 1 mg per eye, such as about per eye: 0.1, 0.2, 0.3, 0.4, 0.5, 0.6, 0.7, 0.8, 0.9 or 1.0 mg.

A preferred AON according to the invention, is for the treatment of a USH2A related disease or condition of an individual. In all embodiments of the invention, the term "treatment" is understood to include the prevention and/or delay of the USH2A related disease or condition. An individual, which may be treated using an AON according to the invention may already have been diagnosed as having a USH2A related disease or condition. Alternatively, an individual which may be treated using an AON according to the invention may not have yet been diagnosed as having a USH2A related disease or condition but may be an individual having an increased risk of developing a USH2A related disease or condition in the future given his or her genetic background. A preferred individual is a human being. In a preferred embodiment the USH2A related disease or condition is Usher Syndrome type II. Accordingly, the invention further provides an AON according to the invention, or a viral vector according to the invention, or a composition according to the invention for use as a medicament, for treating a USH2A related disease or condition requiring modulating splicing of USH2A pre-mRNA and for use as a medicament for the prevention, treatment or delay of a USH2A related disease or condition.

The invention further provides the use of an AON according to the invention, or of a viral vector according to the invention, or a composition according to the invention for the preparation of a medicament, for the preparation of a medicament for treating a USH2A related disease or condition requiring modulating splicing of USH2A pre-mRNA and for the preparation of a medicament for the prevention, treatment or delay of a USH2A related disease or condition. Therefore in a further aspect, there is provided the use of an AON, viral vector or composition as defined herein for the preparation of a medicament, for the preparation of a medicament for treating a condition requiring modulating splicing of USH2A pre-mRNA and for the preparation of a medicament for the prevention, treatment or delay of a USH2A related disease or condition. A treatment in a use or in a method according to the invention is at least once, lasts one week, one month, several months, one year, 2, 3, 4, 5, 6 years or longer, such as lifelong. Each AON as defined herein for use according to the invention may be suitable for direct administration to a cell, tissue and/or an organ in vivo of individuals already affected or at risk of developing USH2A related disease or condition, and may be administered directly in vivo, ex vivo or in vitro. The frequency of administration of an AON, composition, compound or adjunct compound of the invention may depend on several parameters such as the severity of the disease, the age of the patient, the mutation of the patient, the number of AONs (i.e. dose), the formulation of said molecule, the route of administration and so forth. The frequency may vary between daily, weekly, at least once in two weeks, or three weeks or four weeks or five weeks or a longer time period.

Dose ranges of an AON according to the invention are preferably designed on the basis of rising dose studies in clinical trials (in vivo use) for which rigorous protocol requirements exist. An AON as defined herein may be used at a dose which is ranged from 0.01 and 20 mg/kg, preferably from 0.05 and 20 mg/kg. A suitable intravitreal dose would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg. In a preferred embodiment, a concentration of an AON as defined herein, which is ranged from 0.1 nM and 1 µM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nM. If several AONs are used, this concentration or dose may refer to the total concentration or dose of AONs or the concentration or dose of each AON added. In a preferred embodiment, a viral vector, preferably an AAV vector as described earlier herein, as delivery vehicle for a molecule according to the invention, is administered in a dose ranging from $1 \times 10^9$-$1 \times 10^{17}$ virus particles per injection, more preferably from $1 \times 10^{10}$-$1 \times 10^{12}$ virus particles per injection. The ranges of concentration or dose of AONs as given above are preferred concentrations or doses for in vivo, in vitro or ex vivo uses. The skilled person will understand that depending on the AON used, the target cell to be treated, the gene target and its expression levels, the medium used and the transfection and incubation conditions, the concentration or dose of AON used may further vary and may need to be optimized any further.

The invention further provides a method for modulating splicing of USH2A pre-mRNA in a cell comprising contacting the cell, preferably a retina cell, with an AON according to the invention, or a viral vector according to the invention, or a composition according to the invention. The features of this aspect are preferably those defined earlier herein. Contacting the cell with an AON according to the invention, or a viral vector according to the invention, or a composition according to the invention may be performed by any method known by the person skilled in the art. Use of the methods for delivery of AONs, viral vectors and compositions described herein is included. Contacting may be directly or indirectly and may be in vivo, ex vivo or in vitro.

The invention further provides a method for the treatment of a USH2A related disease or condition requiring modulating splicing of USH2A pre-mRNA of an individual in need thereof (such as Usher Syndrome type II), said method comprising contacting a cell, preferably a retina cell, of said individual with an AON according to the invention, or a viral vector according to the invention, or a composition according to the invention. The features of this aspect are preferably those defined earlier herein. Contacting the cell, preferably a retina cell with an AON according to the invention, or a viral vector according to the invention, or a composition according to the invention may be performed by any method known by the person skilled in the art. Use of the methods for delivery of AONs, viral vectors and compositions described herein is included. Contacting may be directly or indirectly and may be in vivo, ex vivo or in vitro. A preferred USH2A related disease or condition is Usher Syndrome type II. Unless otherwise indicated each embodiment as described herein may be combined with another embodiment as described herein.

Figure 4:
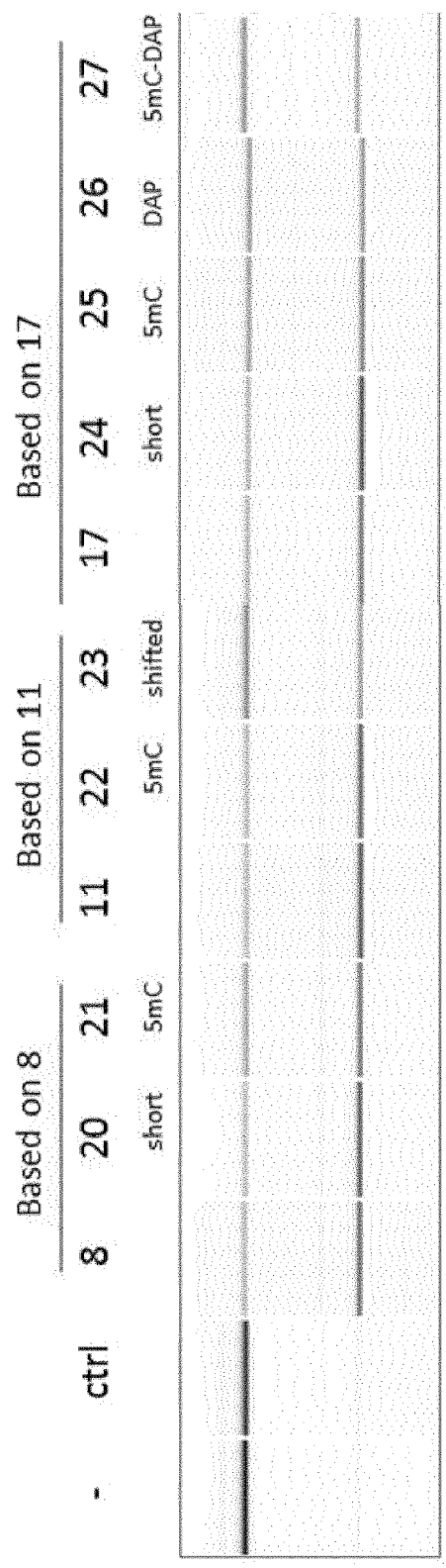
FIG. 4 shows the reverse transcriptase results of the PE40 skip screening of a set of oligonucleotides that were taken one step further and were based on USH2a-PE40-8, -11, and -17. Short means shorter than the original. 5mC means 5-methyl-cytosine (see also Table 1). DAP means 2, 6-diaminopurine.
Figure 5:
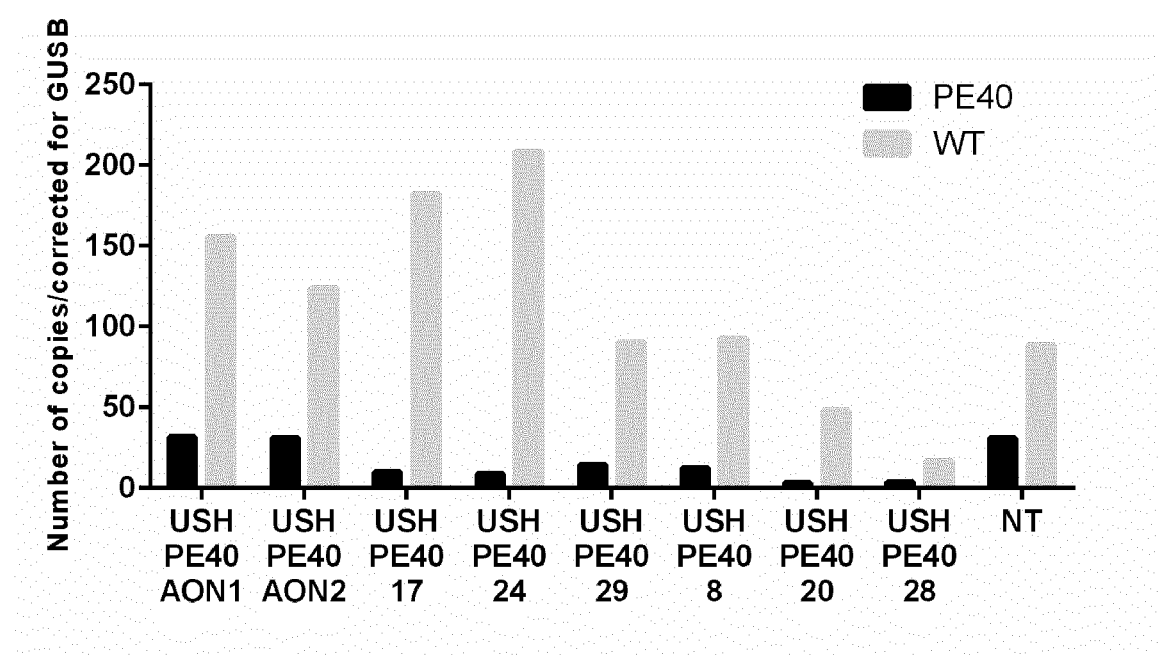
FIG. 5 shows a bar diagram representing the number of droplets expressing PE40 (left bars for each AON) as compared to wild type products (right bars for each AON), corrected for beta-glucuronidase expression from the GUSB gene (housekeeping gene) as a standard, and as frequently used as such by the person skilled in the art, in USH2 patient fibroblasts, treated with eight different oligonucleotides, as outlined in example 1.

The present invention relates to an antisense oligonucleotide (AON) comprising a sequence selected from the group consisting of SEQ ID NO:6, 3, 4, 5, 7, 8, 19, 21, 23, 24, 25, 26, 27, 28, 29, 30, 31, 32, 34, 35, 36, and 37, preferably selected from SEQ ID NO:6, 3, 4, 5, 7, 8, 26, 34, 35, and 37, more preferably selected from SEQ ID NO:6, 3, 4, 5, 7, 8, 26, and 35. The AONs of the present invention are capable of inducing, stimulating or enhancing skipping of pseudo exon 40 (PE40) in the USH2A pre-mRNA, wherein the inclusion of PE40 is due or caused by the c.7595-2144A>G that is frequently found in USH2 patients. It is to be understood, and this is further detailed in the examples, as well as in FIG. 1-5 and in Table 1, that the AONs are not randomly picked but form three 'derivative groups' based on the three new AONs named USH2a-PE40-3, -5 and -7, respectively, as follows:

The AONs based on USH2a-PE40-3 (SEQ ID NO:19) are the AONs of SEQ ID NO: 3, 5, 7, 24, 25, 26, 34, 35, and 36, with USH2a-PE40-8 (SEQ ID NO:3), USH2a-PE40-11 (SEQ ID NO:26), USH2a-PE40-20 (SEQ ID NO:5), USH2a-PE40-22 (SEQ ID NO:35) and USH2a-PE40-28 (SEQ ID NO:7) performing best (see FIGS. 4 and 5).

The AONs based on USH2a-PE40-5 (SEQ ID NO:21) are the AONs of SEQ ID NO:27, 28, and 29.

The AONs based on USH2a-PE40-7 (SEQ ID NO:23) are the AONs of SEQ ID NO:4, 6, 8, 30, 31, 32, and 37, with USH2a-PE40-17 (SEQ ID NO:4), USH2a-PE40-24 (SEQ ID NO:6) and USH2a-PE40-29 (SEQ ID NO:8) performing best (see FIGS. 4 and 5), wherein even USH2a-PE40-17 and -24 outperform all other AONs.

The overlapping sequence that is present in the very effective AONs of SEQ ID NO:6, 4, 8, 23, 30, 31, 32, 37 is 5'-AGAUGAUCUCUUA-3' (SEQ ID NO:42), wherein a Cytosine may be replaced with a 5-methyl-Cytosine (5mC).

The overlapping sequence that is present in the very effective AONs of SEQ ID NO:3, 5, 7, 19, 24, 25, 26, 34, 35, 36 is 5'-CGCUGC-3' (SEQ ID NO:43), wherein a Cytosine may be replaced with a 5-methyl-Cytosine (5mC).

The overlapping sequence that is present in the very effective AONs of SEQ ID NO:21, 27, 28, 29 is 5'-AUUU-CAAUUUCAUGAUUU-3' (SEQ ID NO:44), wherein a Cytosine may be replaced with a 5-methyl-Cytosine (5mC).

The invention therefore also relates to an AON comprising a sequence selected from the group consisting of SEQ ID NO:42, 43 and 44.

The target region of the very effective AONs of SEQ ID NO:6, 4, 8, 23, 30, 31, 32, 37, which includes the splicing boundary at the 3' end of the PE40 sequence is 5'-UCCAAGGUAAGAGAUCAUCUUUAAGAAAAGG-3' (SEQ ID NO:45).

The target region of the very effective AONs of SEQ ID NO:3, 5, 7, 19, 24, 25, 26, 34, 35, 36 is 5'-UCUGCAACAAGAGCAGCGAAUCUACUCAGC-3' (SEQ ID NO:46).

The target region of the very effective AONs of SEQ ID NO:21, 27, 28, 29 is 5'-GGAAACAAAU-CAUGAAAUUGAAAUUGAACA-3' (SEQ ID NO:47).

The shortest AON that targets any sequence of SEQ ID NO:45, 46 and 47 was 18 nucleotides long (USH2a-PE40-23 (SEQ ID NO:36). The invention therefore also relates to an AON that is capable to inducing skipping of pseudo exon 40 (PE40) from human USH2A pre-mRNA, wherein said AON comprises a sequence that is complementary to at least 18, 19, 20, 21, 22, 23, or 24 consecutive nucleotides of SEQ ID NO:45, 46 or 47.

In another embodiment of the invention, it relates to an AON that is able to induce, cause, stimulate, and/or enhance skipping of PE40 from human USH2A pre-mRNA, wherein said AON comprises or consists of a sequence selected from any of the following groups of sequences: (i) SEQ ID NO:6, 4, 8, 23, 30, 31, 32, 37; (ii) SEQ ID NO:3, 5, 7, 19, 24, 25, 26, 34, 35, 36; and (iii) SEQ ID NO:21, 27, 28, 29. In a preferred embodiment, said AON comprises or consists of a sequence selected from any of the following groups of sequences: (i) SEQ ID NO:6, 4, 8; and (ii) SEQ ID NO:3, 5, 7, 26, 35. In a highly preferred embodiment, said AON comprises or consists of a sequence selected from SEQ ID NO: 6 and 4. In a particular aspect, the retention of PE40 in the USH2A pre-mRNA (or the presence of PE40 in the mRNA after splicing has been completed) is due to the c.7595-2144A>G mutation in the USH2A gene, although it cannot be excluded that other (identified or thus far unidentified) mutations in the USH2A gene exist that also cause the presence of PE40 in the USH2A mRNA. Preferably, the AON of the present invention is an oligoribonucleotide (RNA oligonucleotide) that comprises at least one 2'-0 alkyl modification, such as a 2'-O-methyl (2'-O-Me), a 2'-O-ethyl, or a 2'-O-propyl. Another preferred modification is 2'-O-methoxyethyl (2'-O-MOE). In one preferred aspect, all nucleotides in the AON of the present invention are 2'-O-methyl modified. Preferably, the AON of the present invention has at least one phosphorothioate linkage, and more preferably, all sequential nucleotides within the AON of the present invention are interconnected by phosphorothioate linkages.

In a preferred embodiment, the AON of the present invention has a length of 18 to 143 nucleotides, preferably 18 to 40 nucleotides, more preferably 18 to 30 nucleotides, even more preferably 18 to 24 nucleotides. In a preferred aspect, the AON according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives. To increase the therapeutic effect, it may be useful to apply multiple AONs of the present invention. Hence, in another preferred embodiment, the invention relates to a set of AONs, said set comprising at least two AONs according to the invention. In another aspect the invention relates to a viral vector expressing an AON according to the present invention, when placed under conditions conducive to expression of the AON. The invention also relates to a pharmaceutical composition comprising an AON, a set of AONs or a viral vector according to the invention, and a pharmaceutically acceptable excipient. Preferably, said pharmaceutical composition is for intravitreal administration and is dosed in an amount ranged from 0.05 mg and 5 mg of total AON per eye. More preferably, said pharmaceutical composition is for intravitreal administration and is dosed in an amount ranged from 0.1 and 1 mg of total AON per eye, such as about 0.1, 0.2, 0.3, 0.4, 0.5, 0.6, 0.7, 0.8, 0.9 or 1.0 mg of total AONs per eye. In yet another aspect, the invention relates to an AON according to the invention, a set of AONs according to the invention and as claimed herein, a vector according to the invention, or a composition according to the invention, for use as a medicament, preferably for use in the treatment or prevention of a USH2A related disease or condition requiring modulating splicing of USH2A pre-mRNA. In yet another aspect the invention relates to a use of an AON according to the invention, a set of AONs according to the invention, a vector according to the invention or a composition according to the invention, in the preparation of a medicament for treating a USH2A related disease or condition requiring modulating splicing of USH2A pre-mRNA.

The present invention further relates to a method for modulating splicing of USH2A pre-mRNA in a cell, said method comprising contacting said cell with an AON according to the invention, a set according to the invention, a vector according to the invention, or a composition according to the invention. Said cell may be an in vitro cell, an ex vivo cell or an in vivo cell. Said cell used in said method would preferably be present in the eye of, or obtained from, a (human) subject suffering from an USH2A related disorder or being at risk thereof. Hence, in another preferred aspect, the invention relates to a method for the treatment of a USH2A related disease or condition requiring modulating splicing of USH2A pre-mRNA, such as Usher Syndrome type II, in an individual suffering therefrom, said method comprising contacting a cell of said individual with an AON according to the invention, a set according to the invention, a vector according to the invention, or a composition according to the invention.

In yet another aspect, the invention relates to a pseudo exon skipping antisense oligonucleotide according to the invention, a use according to the invention, or a method according to the invention, wherein the USH2A related disease or condition requiring modulating splicing of USH2A is Usher Syndrome Type II. In a most preferred aspect, the pseudo exon that is skipped by using the antisense oligonucleotides of the present invention is the pseudo exon 40 (PE40; SEQ ID NO:9) as disclosed herein.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value. The sequence information as provided herein should not be so narrowly construed as to require inclusion of erroneously identified bases. The skilled person is capable of identifying such erroneously identified bases and knows how to correct for such errors. All patent and literature references cited in the present specification are hereby incorporated by reference in their entirety.

EXAMPLES

Example 1. Selection of Antisense Oligonucleotides Having Improved Exon Skipping Properties The intron USH2A mutation (c.7595-2144A>G) creates a cryptic splice donor site that results in the inclusion of an aberrant exon (PE40) into the USH2A mRNA (see FIG. 1AB of WO 2016/005514). Addition of AONs directed against the aberrant exon would prevent the insertion of this exon by preventing the binding of factors that are essential for splicing such as the U1- and U2 snRNP complexes, and serine-arginine rich proteins, thereby restoring normal USH2A splicing and protein synthesis (FIG. 1C of WO 2016/005514). AONs can target splice sites as well as exon sequences. It has been suggested that a positive correlation exists between the capability of AONs to induce exon skipping and the presence of predicted SC35 splice factor binding sites in the target sequence. To design an AON with high exon-skipping potential, the aberrant USH2A exon (152 nucleotides exon sequence plus 15 nucleotides of intron sequence on each side) was scrutinized for exon splice enhancer binding motifs, using the ESE finder 3.0 program. Within the aberrant exon, two regions with respectively three and two SC35-binding motifs were predicted (data not shown). Hence, two AONs were designed such that it encompassed these regions with SC35 motifs, designated AON1 (SEQ ID NO:1) and AON2 (SEQ ID NO:2), and being complementary to the USH2A mRNA. AON1 and AON2 exon-skipping potential was investigated in WO 2016/005514 (see FIG. 2 therein).

In this example it is shown that even more potent AONs could be identified, generated and used that appear to have even stronger exon-skipping potential than AON1 and AON2 that were previously tested. An overview of all newly tested oligonucleotides is provided in Table 1. All antisense oligonucleotides used herein were purchased from Eurogentec, MicroSynth or TriLink and designed with a Tm of 58° C., and modified with a 2'-O-methyl group at the sugar chain and a phosphorothioate (PS) backbone, and dissolved in phosphate buffered saline before use.

In the first screening step, the effect of the AONs was assayed by using a splicing reporter construct pCI-Neo-USH2a-PE40 (WO 2016/005514). This construct contains the PE40 sequence surrounded by 500 nucleotides of intronic sequence, which has been inserted in an intron between exons 3 and 5 derived from the rhodopsin gene. First the reporter plasmids were transfected into HEK293 cells, followed by a separate AON transfection. Reporter plasmids were transfected using MaxPEI as transfection reagent, and the subsequent AON transfections were performed using the Lipofectamine 2000 reagent (Life Technologies). After 24 hour incubation, cells were harvested and RNA was extracted using the ReliaPrep RNA miniprep kit (Promega), and cDNA was prepared using the Maxima cDNA synthesis kit (Thermo, #EP0734). The inclusion of PE40 into the mature mRNA was analysed by RT-PCR, with primers located in the flanking rhodopsin exons 3 and 5.

FIG. 1 shows the initial screening of USH2a-PE40-1 to -7, which was performed using the reporter construct in HEK293 cells, in comparison to a control oligonucleotide and the two known AONs from WO 2016/005514 (AON1 and AON2). In this initial screen USH2a-PE40-1, -2, -4, and -6 did not show an improvement over PE40 exon skipping as determined with AON1 and AON2 (given as R1 and R2 in this figure respectively). Surprisingly however, USH2a-PE40-3, -5, and -7 were found to be significantly more effective than AON1 and AON2, with USH2a-PE40-7 being the most effective.

FIG. 2 shows the sequence of PE40 (as RNA from 5' to 3') and the positions of complementarity of the AONs tested herein. USH2a-PE40-1 (SEQ ID NO:17), USH2a-PE40-2 (SEQ ID NO:18) and USH2a-PE40-4 (SEQ ID NO:20) overlap with the positions of AON1 (SEQ ID NO:1) and AON2 (SEQ ID NO:2). The binding sites of the more effective USH2a-PE40-3 (SEQ ID NO:19), USH2a-PE40-5 (SEQ ID NO:21) and USH2a-PE40-7 (SEQ ID NO:23) are clearly located in different regions from AON1 and AON2 and overlap with putative ESEs (USH2a-PE40-3 and -5), and with the downstream splice site (USH2a-PE40-7; see also lower panel in FIG. 1). It is noted that the binding site for USH2a-PE40-6 (SEQ ID NO:22) is also outside a region bound by AON1 or AON2, but overlaps the binding site of USH2a-PE40-5 (SEQ ID NO:21), suggesting that the more potent targeting region is located towards the 5' end of the PE40 sequence as far as this area is concerned.

Based on the initial experiment of FIG. 1, that clearly showed that there are other regions within the PE40 sequence that appeared to be more effective 'hotspots' for PE40 skipping than those targeted by the AONs of the art, a further set of AONs was designed based on the three areas identified, also in order to improve ease of synthesis, uptake, efficacy and lowered immunogenicity: AONs were shortened, or shifted so that they would have less internal secondary structure. AONs were further modified by including base changes known to enhance binding affinity: 5-methyl-Cytosine (5mC) instead of Cytosine, and 2, 6-diaminopurine (DAP) instead of Adenine, see Table 1. The 5mC modification was also expected to improve the safety of the AON, as it has been implicated in lowering the immunogenicity of RNA and AONs. USH2a-PE40-8, -9, -10, and -11 were based on USH2a-PE40-3. USH2a-PE40-12, -13, and -14 were based on USH2a-PE40-5. USH2a-PE40-15, -16, -17, and -18 were based on USH2a-PE40-7. USH2a-PE40-20 and -21 were based on USH2a-PE40-8. USH2a-PE40-22 and -23 were based on USH2a-PE40-11. USH2a-PE40-24, -25, -26, and -27 were based on USH2a-PE40-17. The positions of the different newly designed AONs are also provided in FIG. 2. The results with the additional AONs are provided in FIGS. 3 and 4. It shows that DAP modifications resulted in lower efficacy (see USH2a-PE40-26 and -27), and this approach was therefore abandoned. In contrast, 5mC-modified AONs generally had an efficacy similar to the corresponding AONs with normal cytosine. However, minor differences in both directions can be observed: The 5mC-modified USH2a-PE40-21 was slightly less effective than the corresponding USH2a-PE40-8. USH2a-PE40-25 was found to be slightly more effective than the original USH2a-PE40-17. Also, the two AONs that had been shortened by two nucleotides (USH2a-PE40-20 and -24, corresponding to -8 and -17, respectively) showed essentially the same effect as their original longer counterparts. Although not more effective than the original, longer AONs, the shortened versions were considered superior due to the fact that they are easier to synthesize and could potentially have better uptake. Based on this, the most effective AONs from these experiments appear to be the shortened oligonucleotides USH2a-PE40-20 and -24 (SEQ ID NO:5 and 6 respectively), and the 5mC-modified USH2a-PE40-22 (SEQ ID NO:35) and USH2a-PE40-25 (SEQ ID NO:37).

TABLE 1

Sequence details of antisense oligonucleotides as tested herein. PE40-AON1 and PE40-AON2 were described earlier in WO 2016/005514. X = 5-methyl-Cytosine (5mC) instead of Cytosine (C); Z = 2, 6-diaminopurine (DAP) instead of Adenine (A).

| AON name | SEQ ID NO | Sequence (5' to 3') |
|---|---|---|
| PE40-AON1 | 1 | GUGUGAUUCUGGAGAGGAAGCUG |
| PE40-AON2 | 2 | CCCUUAAAAGCCAGCAUACA |
| USH2a-PE40-1 | 17 | GGAGAGGAAGCUGAAAGCAG |
| USH2a-PE40-2 | 18 | GAAGGGUCCUUUAACUUGUG |
| USH2a-PE40-3 | 19 | AGAUUCGCUGCUCUUGUUG |
| USH2a-PE40-4 | 20 | CAUUUUAUUAGCUUCCUGCU |
| USH2a-PE40-5 | 21 | UUCAAUUUCAAUUUCAUGAUUUGU |
| USH2a-PE40-6 | 22 | GAGGUGUUCAAUUUCAAUUUC |
| USH2a-PE40-7 | 23 | CUUAAAGAUGAUCUCUUACCUU |
| USH2a-PE40-8 | 3 | UUCGCUGCUCUUGUUGCAGA |
| USH2a-PE40-9 | 24 | GAUUCGCUGCUCUUGUUGCA |
| USH2a-PE40-10 | 25 | GUAGAUUCGCUGCUCUUGUU |
| USH2a-PE40-11 | 26 | GAGUAGAUUCGCUGCUCUUG |
| USH2a-PE40-12 | 27 | AUUUCAAUUUCAUGAUUUGUUUCC |
| USH2a-PE40-13 | 28 | CAAUUUCAAUUUCAUGAUUUGUUU |
| USH2a-PE40-14 | 29 | UGUUCAAUUUCAAUUUCAUGAUUU |
| USH2a-PE40-15 | 30 | AAGAUGAUCUCUUACCUUGGGA |
| USH2a-PE40-16 | 31 | UAAAGAUGAUCUCUUACCUUGG |
| USH2a-PE40-17 | 4 | UUCUUAAAGAUGAUCUCUUACC |
| USH2a-PE40-18 | 32 | CCUUUUCUUAAAGAUGAUCUCUUA |
| USH2a-PE40-19 | 33 | CAAACCCCCACAAUACACAGC |
| USH2a-PE40-20 | 5 | CGCUGCUCUUGUUGCAGA |

TABLE 1-continued

Sequence details of antisense oligonucleotides as tested herein. PE40-AON1 and PE40-AON2 were described earlier in WO 2016/005514. X = 5-methyl-Cytosine (5mC) instead of Cytosine (C); Z = 2, 6-diaminopurine (DAP) instead of Adenine (A).

| AON name | SEQ ID NO | Sequence (5' to 3') |
|---|---|---|
| USH2a-PE40-21 | 34 | UUXGXUGXUXUUGUUGXAGA |
| USH2a-PE40-22 | 35 | GAGUAGAUUXGXUGXUXUUG |
| USH2a-PE40-23 | 36 | GCUGAGUAGAUUCGCUGC |
| USH2a-PE40-24 | 6 | CUUAAAGAUGAUCUCUUACC |
| USH2a-PE40-25 | 37 | UUXUUAAAGAUGAUXUXUUAXX |
| USH2a-PE40-26 | 38 | UUCUUZZZGZUGZUCUCUUZCC |
| USH2a-PE40-27 | 39 | UUXUUZZZGZUGZUXUXUUZXX |
| USH2a-PE40-28 | 7 | XGXUGXUXUUGUUGXAGA |
| USH2a-PE40-29 | 8 | XUUAAAGAUGAUXUXUUAXX |

USH2a-PE40-8, -17, -20, -24, -28 and -29 (SEQ ID NO:3 to 8) were further tested for their effectiveness in exon skipping capabilities and immunogenicity in vitro. The target nucleotide sequence for oligonucleotides USH2a-PE40-8, -20 and -28 (with which the oligonucleotides (partly) overlap) is as follows: 5'-TCTGCAACAAGAGCAGCGAA-3' (SEQ ID NO:10), located within PE40. The target nucleotide sequence for oligonucleotides USH2a-PE40-17, -24 and -29 (with which the oligonucleotides (partly) overlap) is as follows: 5'-AGG*TAAGAGATCATCTTTAAGAA-3' (SEQ ID NO:11), located partly in PE40 (underlined AG) and its flanking region comprising the c.7595-2144A>G mutation (bold guanosine with asterisk). Fibroblasts were collected from an USH2 patient carrying the USH2A c.7595-2144A>G and c.2391_2392 del compound heterozygous mutation. Cells were kept at 37° C. in DMEM AQ medium containing 20% FBS and 1% NaPyr (Sigma Life Sciences). The cells were plated at a density of $1.0 \times 10^6$ cells/well. The AONs were complexed with Lipofectamine 2000 (Life Technologies, lot: 1699509) in OptiMem (lot: 1697387) for 30 min and then added to the fibroblasts at a concentration of 100 nM. Incubation lasted for a further 24 h. Cells were treated with cycloheximide for 4 h at the end of the incubation period of 24 h to inhibit nonsense-mediated mRNA decay. After 24 h incubation cells were harvested and RNA was extracted using the ReliaPrep RNA miniprep kit (Promega) using the protocol of the manufacturer. Subsequently, cDNA was prepared using the Maxima cDNA synthesis kit (Thermo, #EP0734, lot: 00335736), using the scheme of Table 2 and following the protocols of the manufacturer. The levels of PE40 and wildtype cDNA were determined using a droplet digital PCR (ddPCR) (QX2000 droplet reader) applying the pipetting scheme of Table 3 and primers of Table 4. Data was analyzed by Quanta Life Software and Excel. GUSB (Applied Biosystems, lot: P160210-006 E01) was used as a housekeeping gene, using methods known to the person skilled in the art.

FIG. 5 shows the number of droplets expressing PE40 versus wildtype corrected for GUSB expression levels in patient fibroblasts treated with the eight different AONs together with one non-treated (NT) sample. Clearly, especially AON1, AON2, USH2a-PE40-17 (SEQ ID NO:4) and USH2a-PE40-24 (SEQ ID NO:6), in this FIG. 5 abbreviated to USH-PEO-17 and USH-PE40-24, appeared to be most effective in enhancing the appearance of wildtype levels and outperform the two known oligonucleotides AON1 and AON2, whereas the other four AONs were less effective. Importantly, it was further observed that USH2a-PE40-17 and USH2a-PE40-24 were able to lower PE40 levels, an effect that was not observed with AON1 and AON2, showing that these two new pseudo exon skipping antisense oligonucleotides (USH2a-PE40-17 and USH2a-PE40-24) in this setting perform even better than the two known oligonucleotides. It is further noted that the other four oligonucleotides (USH2a-PE40-8, -20, -28, and -29 also are able to lower PE40 levels in comparison to the two known oligonucleotides AON1 and AON2, which makes that these four oligonucleotides also outperform the oligonucleotides from the art.

TABLE 2 cDNA preparation

| | Per sample Gene specific | Per sample Random Hexam. |
|---|---|---|
| 5X cDNA synthesis buffer | 4 μl | 4 μl |
| dNTP Mix | 2 μl | 2 μl |
| ddPCR.USH2a-PE40.Rv2 | 1 μl | |
| Random Hexamers | | 1 μl |
| Maxima Enzyme Mix | 1 μl | 1 μl |
| Template (150-600 ng RNA) | | |
| Water, nuclease-free | Till 20 μl with water | Till 20 μl with water |
| Total volume | 20 μl | 20 μl |

Gene Specific Primer were Used for Samples and Random Hexamers for GUSB Housekeeping.

TABLE 3

Pipetting scheme ddPCR

| | Experiment | Control |
|---|---|---|
| Supermix for probes | 11 μl | 11 μl |
| Primer 1 | 450 nM | 450 nM |
| Primer 2 | 450 nM | 450 nM |
| Probe 1 | 250 nM | 250 nM |
| Probe 2 | 250 nM | 250 nM |
| Template | Up to 330 ng | 0 μl |
| Water | Add to 22 μl final volume | Add to 22 μl final volume |
| Total | 22 μl per sample | 22 μl per sample |

TABLE 4

Multiplex ddPCR primers and probes ddPCR.USH2a-PE40.Fw1  5'-TCCAATGGATTTGGCAGTGC-3'
SEQ ID NO: 12

TABLE 4-continued

Multiplex ddPCR primers and probes

```
ddPCR.USH2a-PE40.Rv2    5'-GTTCTCAAGTATAGACGGCC-3'
SEQ ID NO: 13 ddPCR.USH2a-PE40.Rv4    5'-GCCAGGTGACCAACATCATT-3
SEQ ID NO: 14 ddPCR.USH2a-PE40.FAM    5'-/56-FAM/CAGCCAGAGCAGGAAGCT/3BHQ_1/3'
SEQ ID NO: 15 ddPCR.USH2a-WT.HEX      5'-/5HEX/GCAGAGGACAAACCTGGA/3BHQ_1/3'
SEQ ID NO: 16
```

Example 2. In Vitro Toxicity of the New Antisense Oligonucleotides

Oligonucleotides have the potential to cause activation of so-called pattern recognition receptors (PRR) of the vertebrate innate immune system (Bauer et al. 2008. Immunobiology 213:315-328). The most well studied family of PRR receptors are the toll-like receptors (TLRs). TLRs are a class of proteins that play a key role in the innate immune system. They are single, membrane-spanning, non-catalytic receptors that are usually expressed in macrophages and dendritic cells that recognize structurally-conserved molecules derived from microbes. TLRs that are activated by different types of nucleic acids are those located on endosomes: TLR3 recognizes double stranded RNA; TLR7/8 recognizes double and single stranded RNA.

Upon recognition of these components by the PRRs, a specific 'antimicrobial' immune response is triggered. TLR activation results in the activation of nuclear factor kappa-light-chain-enhancer of activated B cells (NF-κB), Interferon regulatory factor 3 (IRF-3) and activator protein 1 (AP-1) (Kawasaki 2014. Front Immunol 25:461). Activation of AP-1, IRF-3 and NF-κB results in the production of inflammatory cytokines, type-I interferons and other mediators of the innate immune response. These processes not only trigger immediate host defensive responses such as inflammation, but also prime and orchestrate antigen-specific adaptive immune responses. In vitro exposure of primary human peripheral blood mononuclear cells (PBMC) was used to assess (systemic) drug-specific immune responses and immunotoxicity, as described earlier (Lankveld 2010. Methods Mol Biol 598:401-423). The in vitro assay using PBMC is an established preclinical test using the production of (inflammatory) cytokines as surrogate marker for systemic immune responses. The PBMC assay enables prediction of tolerability as a factor of the immunogenicity and allergenicity potential of investigational compounds, and could enable an estimation of a safe dosing range for these compounds.

For studying USH2a PE40-20, USH2a PE40-24, USH2a PE40-28 and USH2a PE40-29 in-house isolated PBMC were used, acquired from buffy coats of healthy blood bank donors. Production of the key pro-inflammatory cytokines in the culture supernatant was assessed after 24 h of stimulation with oligonucleotides at concentrations of 1 and 4 µM. Moreover, the viability of the PBMCs after treatment with the oligonucleotides was analyzed by measuring the fluorescent resorufin in the culture supernatant to assess potential cytoxic effect of USH2a-PE40 AONs. Viable cells convert the non-fluorescent resazurin into fluorescent resorufin (O'Brien et al. 2000. Eur J Biochem 267:5421-5426).

Figure 6:
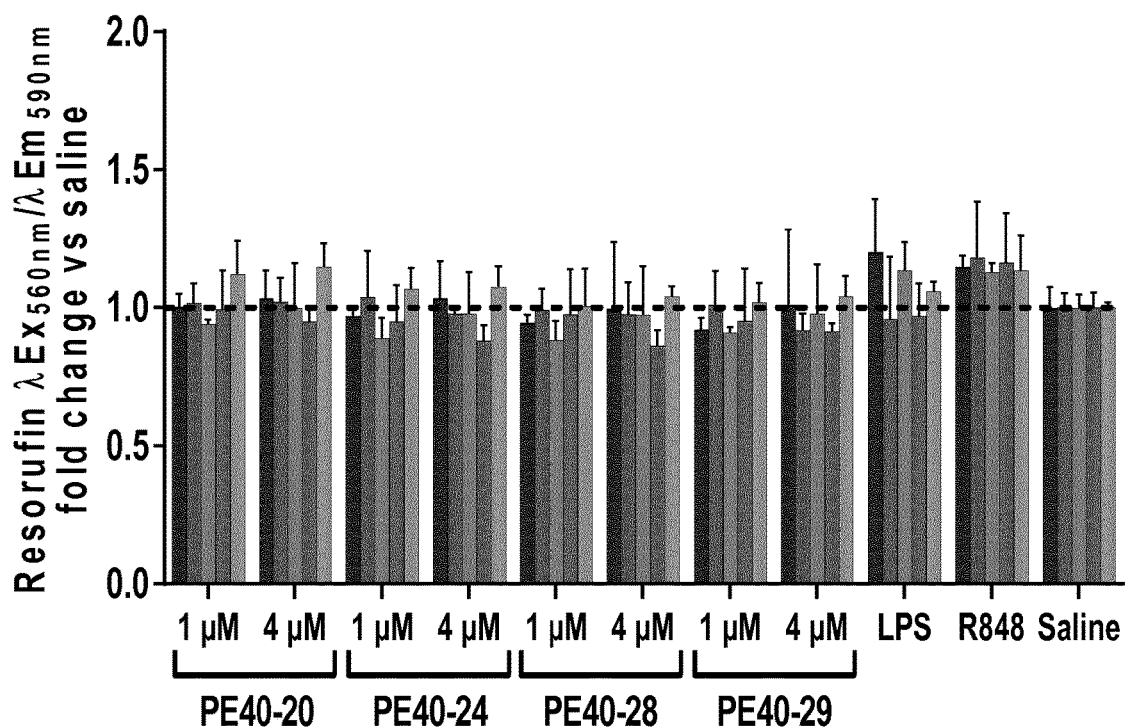
FIG. 6 shows the results of an immunogenicity and immunotoxicity assessment of the indicated USH2a-PE40 AONs in human PBMCs. A. Heat map depicting the fold changes and significance levels of cytokine concentrations in culture supernatant after 24 h stimulation of human PBMCs with oligonucleotides as disclosed herein, or the positive controls LPS (100 ng/ml) and R848 (1 µM) compared to saline-treated human PBMCs. Every square shows the fold change per treatment condition for each measured cytokine. B. Relative number of viable PBMCs expressed as fold change of Resorufin fluorescence compared to saline treated PBMCs after 24 h exposure to four different USH2a-PE40 antisense oligonucleotides of the present invention, or the positive controls. Viable cell assessment was performed using the CellTiter-Blue® kit (Promega) using the protocols of the manufacturer. For all individual biological replicates, fold changes were calculated by normalizing measured RFU against geometric mean of corresponding triplicate saline control. Results are shown per individual donor as the mean±SEM of the triplicate fold change, normalized against the mean of its corresponding saline control (dotted line). Repeated measures One-way ANOVA with Dunnett test for multiple corrections (compared to saline) was performed.

Stimulation of human PBMCs with the positive controls LPS (TLR4 agonist) at 100 ng/ml and R848 (TLR7/8 agonist) at 1 µM, resulted in significantly increased concentrations of all measured cytokines, MCP-1, in the culture supernatant. Moreover, stimulation with R848 induced a similar pattern of cytokines, although to a lesser extent. A heat map depicting the significance levels of cytokine concentrations in culture supernatant after stimulation with the oligonucleotides of the present invention or the positive controls compared to saline-treated human PBMC is shown in FIG. 6A. Importantly, stimulation of human PBMCs with the oligonucleotides of the present invention at a concentration of 1 and 4 µM did not result in increased concentrations or results in very minor increased concentrations of any of the measured cytokines in the culture supernatant. Finally, there were no signs of cytotoxicity 24 h after treatment with the oligonucleotides (FIG. 6B).

Example 3. PE40 Skipping in USH2A Pre-mRNA in Optic Cups Generated from an USH2 Patient Retinas cannot be obtained from USH2 patients and used for in vitro studies for obvious reasons. As an alternative for such pre-clinical investigations, it is possible to generate organoids that resemble such patient retina material, herein referred to as optic cups and sometimes also referred to as eye cups. Fibroblasts from Usher Syndrome type II patients, having the USH2A c.7595-2144A>G (p.Lys2532Thrfs*56) and c.2299delG (p.Glu767Serfs*21) mutations in compound heterozygosity were used for optic cup generation. Fibroblasts were reprogrammed using four lentiviruses expressing Oct3/4, Sox2, Klf4 and c-Myc and generously provided by the Radboud UMC Stem Cell Technology Center. Clones were cryopreserved around passage 6 and further analysed for expression of the pluripotent stem cell markers SSEA-4, NANOG, TRA1-81 and OCT3/4 by immunocytochemistry. In total 3 individual clones were generated and stored. These clones passed all defined quality controls (activation of stem cell markers (RT-qPCR) and expression of stem cell and pluripotency markers (IHC) (data not shown). The iPSC line was cultured into optic cups as described previously (Zhong et al 2014. Nature Comm 5:4047; 1-12). iPSCs were differentiated into small clumps and cultured in suspension with mTeSR1 medium and 10 µM Blebbistatin (Sigma) to induce aggregate formation. Aggregates were transitioned into neural-induction medium containing DMEM/F12, 1% N2 supplement, 1× minimum essential media-non-essential amino acids, 2 µg ml$^{-1}$ heparin (Sigma). Aggregates were seeded onto Matrigel-coated dishes. The medium was changed daily. After four weeks of differentiation, neural retina domains were manually detached and cultured in suspension in DMEM/F12 medium supplemented with 2% B27, 1×NEAA, and 1% antibiotic-antimycotic, in a humidified incubator at 37 degrees Celcius. The medium was changed twice a week. In the incubator they gradually formed 3D optic cups. After successful generation of iPSC-derived optic cups, they were treated with USH2a-PE40-24 for one month at 2 µM and 10 µM by refreshing the medium containing the AON every other day. USH2A transcript analysis was performed to determine the inclusion of PE40 into the mature mRNA, with primers 5'-GCTCTCCCAGA-TACCAACTCC-3' (SEQ ID NO:40) and 5"-GATTCACAT-GCCTGACCCTC-3' (SEQ ID NO:41) located in the flanking exons 39 and 42 respectively. Total RNA was isolated from iPSCs and optic cups using the Nucleospin RNA II isolation kit (MACHEREY-NAGEL #740955.50, Düren—Germany), according to the provided protocol. Subsequently, 0.5-1.0 µg of total RNA was used for cDNA synthesis with SuperScript VILO reverse transcriptase kit (ThermoFisher Scientific; cat.#11755050; lot.#1718541).

USH2A, LIN28A, OCT3/4, NANOG and SOX2 were subsequently amplified using forward and reverse primers. The housekeeping gene GUSB was used as a reference. GoTaq (Promega A6001) was used to amplify USH2A, LIN28A, OCT3/4, NANOG, SOX2 and GUSB cDNA in triplicate in a qPCR machine. Non-treated optic cups would reveal a wild-type band (900 bp) and a band containing the PE40 sequence (1052 bp), which is easily distinguished in gel.

Figure 7:
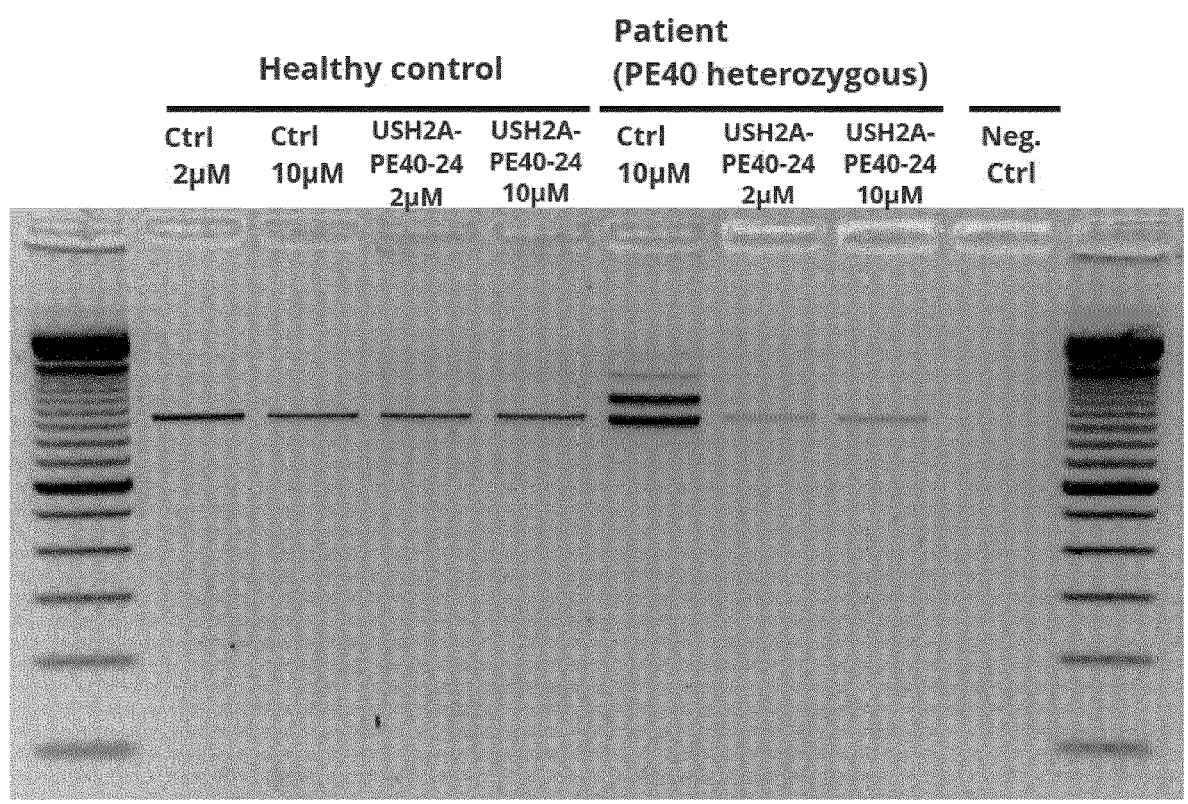
FIG. 7 shows the results of PE40 skipping in USH2A pre-mRNA in optic cups generated from fibroblasts obtained from a heterozygous USH2 patient after treatment with USH2a-PE40-24. The four left lanes show the results in optic cups generated from fibroblasts from a healthy donor, and the subsequent three lanes show the results with optic cups from the USH2 patient fibroblasts. The control oligonucleotide is an unrelated oligonucleotide not complementary to USH2A pre-mRNA. The negative control on the right does not contain nucleic acid material. The control lane 5 shows two dominant bands, the upper band representing the mRNA comprising the PE40 sequence and the lower fat band representing the mRNA lacking the PE40 sequence. Treatment with USH2a-PE40-24 results in complete skipping of PE40 from the pre-mRNA as no upper bands were detectable.

The result as provided in FIG. 7 shows that both concentrations (2 µM and 10 µM) of oligonucleotide USH2a-PE40-24 (SEQ ID NO:6) when used on the optic cups generated from USH2 patient fibroblasts, were sufficient to induce the complete skipping of PE40, as no transcript could be detected comprising PE40. It is unclear what the ultimate upper non-specific faint band is in the ctrl lane.

From these results it is concluded that an antisense oligonucleotide, and in this particular case USH2a-PE40-24, is capable of efficiently skipping PE40 from USH2A pre-mRNA in organoids that resemble the retina of a (heterozygous PE40) patient suffering from Usher Syndrome type II.

The invention claimed is:

1. An antisense oligonucleotide (AON) that comprises a sequence selected from any of the following groups of sequences:
   (i) SEQ ID NO:6, 4, 8, 23, 30, 31, 32, 37;
   (ii) SEQ ID NO:3, 5, 7, 19, 24, 25, 26, 34, 35, 36; and
   (iii) SEQ ID NO:21, 27, 28, 29.

2. An AON according to claim 1, wherein said AON is an oligoribonucleotide (RNA oligonucleotide) comprising at least one 2'-0 alkyl modification, such as a 2'-O-methyl, a 2'-O-ethyl, or a 2'-O-propyl.

3. An AON according to claim 2, wherein all nucleotides in said AON are 2'-O-methyl modified.

4. An AON according to claim 1, wherein said AON has at least one phosphorothioate linkage.

5. An AON according to claim 4, wherein all sequential nucleotides are interconnected by phosphorothioate linkages.

6. A viral vector expressing an AON as defined in claim 1, when placed under conditions conducive to expression of the AON.

7. A pharmaceutical composition comprising an AON according to claim 1, and a pharmaceutically acceptable excipient, wherein the pharmaceutical composition is for intravitreal administration.

8. A pharmaceutical composition according to claim 7, wherein the pharmaceutical composition is for intravitreal administration and is in an amount ranging from 0.05 mg to 5 mg.

9. A method for skipping PE40 from human USH2A pre-mRNA in a cell, said method comprising administering to said cell an AON according to claim 1, and allowing the AON to induce, cause or stimulate skipping of PE40 from the human USH2A pre-mRNA.

10. A method for the treatment of an USH2A-related disease, or a condition requiring the skip of PE40 from the USH2A pre-mRNA in an individual suffering therefrom, said method comprising administering to said individual an effective amount of an AON according to claim 1.

11. The method according to claim 10, wherein the USH2A-related disease or the condition requiring the skip of PE40 from the USH2A pre-mRNA is Usher Syndrome Type II.

12. A pharmaceutical composition comprising a viral vector according to claim 6 and a pharmaceutically acceptable excipient, wherein the pharmaceutical composition is for intravitreal administration.

13. The method of claim 9 or 10 wherein said administering of said AON is by administering a viral vector encoding said AON.

14. The method of claim 10 wherein said administering is intravitreal administration.

15. An AON according to claim 1, wherein said AON is an oligoribonucleotide (RNA oligonucleotide) comprising one or more 2'-0 methoxyethyl modifications.

* * * * *